United States Patent [19]
Cary et al.

[11] Patent Number: 5,596,124
[45] Date of Patent: Jan. 21, 1997

[54] METHOD FOR SAFENING HERBICIDES IN CEREAL CROPS USING 5-ARYLOXY-1,2-(DISUBSTITUTED)BENZENE COMPOUNDS

[75] Inventors: Gail E. Cary, Lawrenceville; Peter J. Wepplo, Princeton, both of N.J.; Barbara A. Bench, Providence, R.I.

[73] Assignee: American Cyanamid Company, Madison, N.J.

[21] Appl. No.: 353,029

[22] Filed: Dec. 9, 1994

[51] Int. Cl.$^6$ ........................................... C07L 9/76
[52] U.S. Cl. .............................. 560/61; 560/53; 549/318; 504/105; 504/110
[58] Field of Search ..................... 560/61, 53; 504/105, 504/110; 549/318

[56] References Cited

U.S. PATENT DOCUMENTS

| | | |
|---|---|---|
| 4,242,121 | 12/1980 | Hawkins et al. . |
| 4,309,210 | 1/1982 | Quadranti et al. . |
| 4,414,020 | 11/1983 | Heier et al. . |
| 4,465,508 | 8/1984 | Barton et al. . |
| 4,780,128 | 10/1988 | Cartwright . |
| 4,845,264 | 7/1989 | Azuma et al. . |

FOREIGN PATENT DOCUMENTS

| | | |
|---|---|---|
| 0023392 | 4/1981 | European Pat. Off. . |
| 0075377 | 3/1996 | European Pat. Off. . |

*Primary Examiner*—Paul J. Killos
*Attorney, Agent, or Firm*—John W. Hogan, Jr.

[57] ABSTRACT

There is provided a method for safening herbicides in cereal crop plants by using 5-aryloxy-1,2-(disubstituted)benzene compounds of formula I

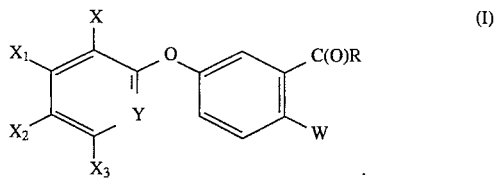

Further provided are compositions comprising a 5-aryloxy-1,2-(disubstituted)benzene compound of formula I.

20 Claims, No Drawings

METHOD FOR SAFENING HERBICIDES IN CEREAL CROPS USING 5-ARYLOXY-1,2-(DISUBSTITUTED)BENZENE COMPOUNDS

BACKGROUND OF THE INVENTION

One of the most common practices for controlling undesirable plant species is the use of herbicides. However, it is known that when certain herbicides are applied in effective amounts they may also damage the crop plants. For example, certain herbicides which are effective against certain annual and perennial grass weeds cannot be used in all crops, especially cereal crops such as corn, wheat, sorghum, oat, barley and rice because the herbicide injures the crops as well as controls the weeds.

Therefore, research efforts continue to discover and develop compounds which reduce or eliminate herbicidal injury to cereal crops.

U.S. Pat. Nos. 4,309,210 and 4,414,020 describe methods for safening crops from injury caused by herbicides. However, the safener compounds disclosed in those patents are outside the scope of the present invention.

It is an object of the present invention to provide a method for protecting cereal crops from injury caused by a herbicidally effective amount of a herbicide.

It is also an object of this invention to provide safener compositions.

Those and other objects of the present invention will become more apparent from the detailed description thereof set forth below.

SUMMARY OF THE INVENTION

The present invention relates to a method for protecting cereal crops from injury caused by a herbicidally effective amount of a herbicide which comprises applying to the cereal crop plant, the seed of the cereal crop, or the soil or water surrounding the cereal crop or cereal crop seed an effective antidotal amount of a 5-aryloxy-1,2-(disubstituted)benzene compound of formula I

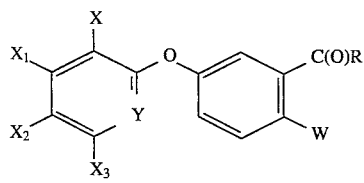

wherein

Y is N or $CX_4$;

X, $X_1$, $X_2$, $X_3$ and $X_4$ are each independently hydrogen, halogen, $C_1$–$C_4$alkyl, $C_1$–$C_4$haloalkyl, $C_1$–$C_4$-alkoxy or $C_1$–$C_4$haloalkoxy;

W is $O(CR_1R_2)_nC(O)R_3$, $CR_4=CR_5C(O)R_6$ or

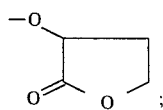

R, $R_3$ and $R_6$ are each independently $OR_7$ or $R_8$;

$R_7$ is hydrogen, $C_1$–$C_4$alkyl, $C_2$–$C_6$alkenyl, $C_2$–$C_6$alkynyl, furfuryl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_8$ is hydrogen, $C_1$–$C_4$alkyl, $C_2$–$C_6$alkenyl, $C_2$–$C_6$alkynyl, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_1$ is hydrogen, halogen, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $C_1$–$C_{12}$alkyl optionally substituted with phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_2$, $R_4$ and $R_5$ are each independently hydrogen, halogen or $C_1$–$C_4$alkyl;

n is an integer of 1, 2, 3 or 4; or when $R_1$ and $R_2$ are not the same, the optical isomers thereof.

This invention further relates to safener compositions which safen herbicides to cereal crops, but do not safen herbicides to weeds.

DETAILED DESCRIPTION OF THE INVENTION

The present invention provides a method for safening herbicides by applying a chemical safener, a 5-aryloxy-1,2-(disubstituted)benzene compound of formula I, to the seed of the cereal crop, the foliage of the cereal crop or the soil or water surrounding the cereal crop or cereal crop seed.

The safener compounds useful in the method and compositions of the present invention have the following structural formula I

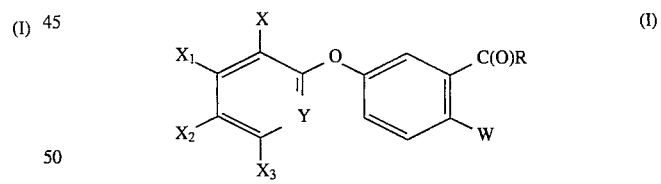

wherein X, $X_1$, $X_2$, $X_3$, Y, R and W are as described hereinabove for formula I.

Preferred safener compounds of the present invention are those wherein

Y is $CX_4$;

X, $X_1$, $X_2$, $X_3$ and $X_4$ are each independently hydrogen, halogen or $C_1$–$C_4$haloalkyl;

W is $O(CR_1R_2)C(O)R_3$;

R is $OR_7$;

$R_3$ is $OR_7$ or $R_8$;

$R_7$ is hydrogen, $C_1$–$C_4$alkyl, $C_2$–$C_6$alkenyl, $C_2$–$C_6$alkynyl, furfuryl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_8$ is $C_1$–$C_4$alkyl;

$R_1$ is hydrogen, halogen, phenyl or $C_1$–$C_{12}$alkyl optionally substituted with phenyl; and $R_2$ is hydrogen or $C_1$–$C_4$alkyl.

More preferred safener compounds of the present invention are those wherein

Y is $CX_4$;

X, $X_3$ and $X_4$ are each independently hydrogen or halogen;

$X_1$ and $X_2$ are each independently hydrogen, halogen or $CF_3$;

W is $O(CHR_1)C(O)R_3$;

R is $OR_7$;

$R_3$ is $OR_7$ or $R_8$;

$R_7$ is hydrogen, $C_1$–$C_4$alkyl, $C_2$–$C_6$alkenyl or an alkali metal, alkaline earth metal, ammonium or organic ammonium cation;

$R_8$ is $C_1$–$C_4$alkyl; and $R_1$ is hydrogen or $C_1$–$C_6$alkyl optionally substituted with phenyl.

5-Aryloxy-1,2-(disubstituted)benzene compounds which are particularly useful for protecting cereal crops from injury caused by a herbicide include α-carboxy-5-[(2-chloro-α,α,α-trifluoro -p-tolyl)oxy]-o-anisic acid, dimethyl ester;

2-(1-carboxybutoxy)-5-[(2-chloro-α, α,α-trifluoro-p-tolyl)oxy]benzoic acid;

2-(1-carboxyethoxy)-5-[(2-chloro-α, α,α-trifluoro-p-tolyl)oxy]benzoic acid;

2-(carboxymethoxy)-5-[(5,6-dichloro-α,α, α-trifluoro-m-tolyl)oxy]benzoic acid, dimethyl ester;

5-[(2-chloro-α,α,α-trifluoro-p-tolyl)oxy]-2-(2-oxopropoxy)benzoic acid, methyl ester;

2-(carboxymethoxy)-5-[(5,6-dichloro-α,α, α-trifluoro-m-tolyl)oxy]benzoic acid;

2-(carboxymethoxy)-5-[(2-chloro-α,α,α-trifluoro-p-tolyl)oxy]benzoic acid, diethyl ester;

2-(carboxymethoxy)-5-[(α,α,α-trifluoro-p -tolyl)oxy] benzoic acid, dimethyl ester;

2-(1-carboxyethoxy)-5-[(2-chloro-α, α,α-trifluoro-p-tolyl)oxy]benzoic acid, dimethyl ester;

2-(carboxymethoxy)-5-[(α,α,α-trifluoro-p -tolyl)oxy] benzoic acid;

2-(carboxymethoxy)-5-[(2-chloro-α,α,α-trifluoro-p-tolyl)oxy]benzoic acid, diallyl ester;

2-(carboxymethoxy)-5-[(2-chloro-α,α,α-trifluoro-p-tolyl)oxy]benzoic acid, diisopropyl ester;

2-[(1-carboxyhexyl)oxy]-5-[(2-chloro -α,α,α-trifluoro-p-tolyl)oxy]benzoic acid;

2-(1-carboxy-3-phenylpropoxy)-5-[(2-chloro-α,α,α-trifluoro-p-tolyl)oxy]benzoic acid;

2-(1-carboxy-3-methylpropoxy)-5-[(2-chloro-α,α,α-trifluoro-p-tolyl)oxy]benzoic acid; and 2-(1-carboxypropoxy)-5-[(2-chloro-α, α,α-trifluoro-p-tolyl)oxy]benzoic acid, among others.

Exemplary of halogen hereinabove are fluorine, chlorine, bromine and iodine. The term "$C_1$–$C_4$haloalkyl" is defined as a $C_1$–$C_4$alkyl group substituted with one or more halogen atoms. The term "$C_1$–$C_4$haloalkoxy" is defined as a $C_1$–$C_4$alkoxy group substituted with one or more halogen atoms. In formula I above, alkali metals include: sodium, potassium and lithium. Alkaline earth metals of formula I include magnesium and calcium. Further, the term "organic ammonium" is defined as a group consisting of a positively charged nitrogen atom joined to from one to four aliphatic groups, each containing from one to sixteen carbon atoms.

Certain 5-aryloxy-1,2-(disubstituted)benzene compounds of formula I may be prepared as shown in Flow Diagram I.

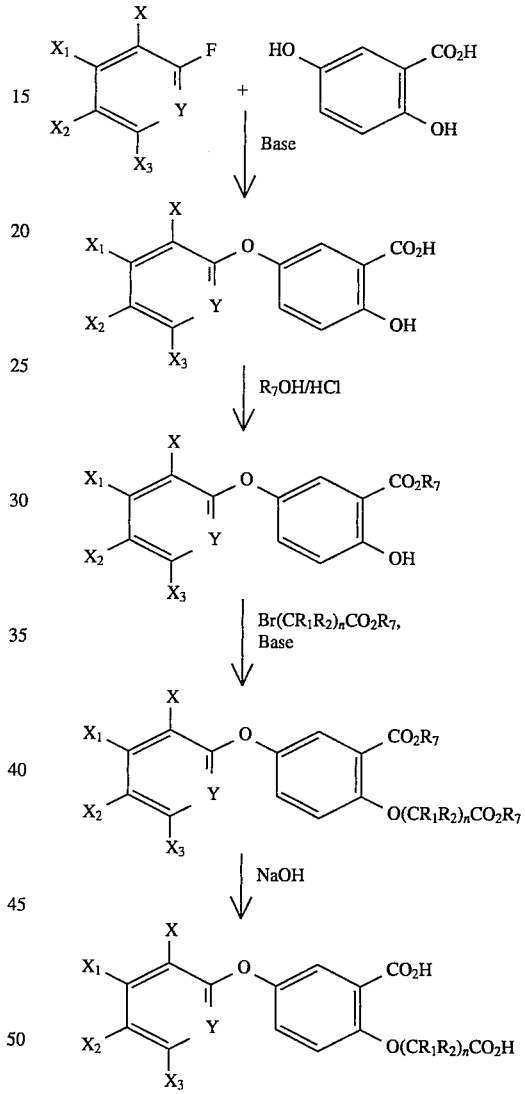

wherein Y, X, $X_1$, $X_2$, $X_3$, $R_1$, $R_2$ and n are as described hereinabove for formula I and $R_7$ is $C_1$–$C_4$alkyl, $C_2$–$C_6$alkenyl, $C_2$–$C_6$alkynyl, furfuryl, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups.

Other methods for the preparation of formula I compounds will become apparent from the examples set forth below.

Uniquely, it has been found that the 5-aryloxy-1,2-(disubstituted)benzene compounds of formula I are useful for protecting cereal crops such as corn, wheat, sorghum, oat, barley and rice from injury caused by a herbicidally effective amount of a herbicide.

Herbicides which may be safened by the formula I compounds include imidazolinone herbicides such as 5-ethyl-2-(4-isopropyl-4-methyl-5-oxo-2-imidazolin-2-yl)-nicotinic acid;

2-(4-isopropyl-4-methyl-5-oxo-2-imidazolin-2-yl)-3-quinolinecarboxylic acid;

isopropylammonium 2-(4-isopropyl-4-methyl-5-oxo-2-imidazolin-2-yl)nicotinate;

methyl 2-(4-isopropyl-4-methyl-5-oxo-2-imidazolin-2-yl)nicotinate;

2-(4-isopropyl-4-methyl-5-oxo-2-imidazolin-2-yl)-5-(methoxymethyl)nicotinic acid;

mixture of methyl 2-(4-isopropyl-4-methyl-5-oxo-2-imidazolin-2-yl)-p-toluate and methyl 6-(4-isopropyl-4-methyl-5-oxo-2-imidazolin-2-yl)-m-toluate; and 2-(4-isopropyl-4-methyl-5-oxo-2-imidazolin-2-yl)-5-methylnicotinic acid;

dinitroaniline herbicides such as

N-(1-ethylpropyl)-2,6-dinitro-3,4-xylidine;

α,α,α-trifluoro-2,6-dinitro-N,N-dipropyl-p-toluidine;

3,5-dinitro-$N^4$,$N^4$-dipropylsulfanilamide;

N-butyl-N-ethyl-α,α,α-trifluoro-2,6-dinitro-p-toluidine;

2,6-dinitro-N,N-dipropylcumidine; and

N-ethyl-α,α,α-trtifluoro-N-(2-methylallyl)-2,6-dinitro-p-toluidine;

sulfonylurea herbicides such as methyl o-{{3-[4,6-bis(difluoromethoxy)-2-pyrimidinyl]ureido}sulfonyl}benzoate;

1-[(o-chlorophenyl)sulfonyl]-3-(4-methoxy-6-methyl-s-triazin-2-yl)urea;

methyl o-{{[3-(4,6-dimethoxy-2-pyrimidinyl)-ureido]sulfonyl}methyl}benzoate;

methyl o-{[3-(4-methoxy-6-methyl-1,3,5-triazin-2-yl)ureido]sulfonyl}benzoate;

1-(4,6-dimethoxy-2-pyrimidinyl)-3-{[3-(dimethylcarbamoyl)-2-pyridyl]sulfonyl}urea;

ethyl o-{[(4-chloro-6-methoxy-2-pyrimidinyl)-carbamoyl]sulfamoyl}benzoate;

ethyl 5-{[3-(4,6-dimethoxy-2-pyrimidinyl)-ureido]sulfonyl}-1-methylpyrazole-4-carboxylate;

methyl 3-{[3-(4-methoxy-6-methyl-1,3,5-triazin-2-yl)ureido]sulfonyl}-2-thiophenecarboxylate; and 1-{[o-(3-chloropropoxy)phenyl]sulfonyl}-3-(4-methoxy-6-methyl-1,3,5-triazin-2-yl)urea;

sulfamoylurea herbicides such as

1-{[o-(cyclopropylcarbonyl)phenyl]sulfamoyl}-3-(4,6-dimethoxy-2-pyrimidinyl)urea;

1-[(o-acetylphenyl)sulfamoyl]-3-(4-methoxy-6-methyl-2-pyrimidinyl)urea; and

1-[(o-acetylphenyl)sulfamoyl]-3-(4,6-dimethoxy-2-pyrimidinyl)urea;

oxime herbicides such as 2-(O-ethyloxime) of 2-butyryl-5-[2-(ethylthio)propyl]-3-hydroxy-2-cyclohexen-1-one;

sodium salt of methyl 5-butyryl-2,2-dimethyl-4,6-dioxocyclohexanecarboxylate 5-(O-allyloxime);

2-[O-(3-chloroallyl)oxime of 5-[2-(ethylthio)propyl]-3-hydroxy-2-propionyl-2-cyclohexen-1-one;

2-(O-ethyloxime) of 2-butyryl-3-hydroxy-5-(tetrahydro-2H-thiopyran-3-yl)-2-cyclohexen-1-one; and 2-(O-ethyloxime) of 3-hydroxy-2-propionyl-5-(2,4,6-trimethylphenyl)-2-cyclohexen-1-one;

2-(4-aryloxyphenoxy)propionic acid herbicides such as methyl 2-{p-{[3-chloro-5-(trifluoromethyl)-2-pyridyl]oxy}phenoxy}propionate;

methyl 2-[p-(2,4-dichlorophenoxy)phenoxy]-propionate;

butyl 2-{p-{[5-(trifluoromethyl)-2-pyridyl]oxy}phenoxy}propionate;

butyl 2-{p-{[5-(trifluoromethyl)-2-pyridyl]oxy}phenoxy}propionate, (R)-;

2-ethoxyethyl 2-{p-{[3-chloro-5-(trifluoromethyl)-2-pyridyl]oxy}phenoxy}propionate;

1-{2-{p-[(3,5-dichloro-2-pyridyl)oxy]phenoxy}propionyl}isoxazolidine;

2-[(isopropylideneamino)oxy]ethyl 2-{p-[(6-chloro-2-quinoxalinyl)oxy]phenoxy}propionate, (R)-;

ethyl 2-{p-[(6-chloro-2-quinoxalinyl)oxy]phenoxy}propionate;

ethyl 2-{p-[(6-chloro-2-benzoxazolyl)oxy]phenoxy}propionate;

N-benzoyl-N-(3,4-dichlorophenyl)alanine, ethyl ester;

2-[(2,4-dichloro-m-tolyl)oxy]-2-methylpropionanilide;

ethyl 2-{p-[(6-chloro-2-benzoxazolyl)oxy]phenoxy}propionate;

ethyl 2-{p-[(6-chloro-2-benzothiazolyl)oxy]phenoxy}propionate;

N-benzoyl-N-(3-chloro-4-fluorophenyl)alanine, isopropyl ester;

N-benzoyl-N-(3-chloro-4-fluorophenyl)alanine, methyl ester; and methyl p,α-dichlorohydrocinnamate;

thiocarbamate herbicides such as ethyl dipropylthiolcarbamate;

S-ethyl diisobutylthiocarbamate;

S-propyl dipropylthiocarbamate;

S-ethyl hexahydro-1H-azepine-1-carbothioate;

S-(p-chlorobenzyl) diethylthiocarbamate; and

S-benzyl bis(1-methylpropyl)thiocarbamate.

2-chloroacetanilide herbicides such as 2-chloro-6'-ethyl-N-(2-methoxy-1-methylethyl)-o-acetotoluidide;

2-chloro-2',6'-diethyl-N-(methoxymethyl) acetanilide;

N-(butoxymethyl)-2-chloro-2'-ethylacetanilide;

2-chloro-2',6'-diethyl-N-(2-propoxyethyl) acetanilide; and 2-chloro-N-isopropylacetanilide; and isoxazolyl-2-imidazolidinone herbicides such as 3-(5-tert-butyl-3-isoxazolyl)-4-hydroxy-1-methyl-2-imidazolidinone; and 3-(5-tert-butyl-3-isoxazoyl)-1-methyl-2-oxo-4-imidazolidinyl methyl carbamate, among others.

Although many of these herbicides have been used with success in certain crops, they have been found to be phytotoxic in other crops, especially cereal crops. Surprisingly, it has been found that by applying a 5-aryloxy-1,2-(disubstituted)benzene compound of formula I to the seed of the cereal crop, the foliage of the cereal crop or the soil or water surrounding the cereal crop or cereal crop seed, the herbicide is safened.

In a first preferred method of the present invention, a corn plant is safened from injury caused by a herbicidally effective amount of an imidazolinone compound, a dinitroaniline compound, a sulfonylurea compound, a sulfamoylurea compound, an oxime compound, a 2-(4-aryloxyphenoxy)propionic acid compound, a thiocarbamate compound, a 2-chloroacetanilide compound or an isoxazolyl-2-imidazolidinone compound by applying to the corn plant or seed of the corn plant an effective antidotal amount of a safener compound of formula I.

The method of the present invention is particularly useful for safening corn from injury caused by a herbicidally effective amount of 5-ethyl-2-(4-isopropyl-4-methyl-5-oxo-2-imidazolin-2-yl)nicotinic acid, 2-(4-isopropyl-4-methyl-5-oxo-2-imidazolin-2-yl)-3-quinolinecarboxylic acid, methyl 2-(4-isopropyl-4-methyl-5-oxo-2-imidazolin-2-yl)nicotinate, 2-(4-isopropyl-4-methyl-5-oxo-2-imidazolin-2-yl)-5-(methoxymethyl)nicotinic acid, mixture of methyl 2-(4-isopropyl-4-methyl-5-oxo-2-imidazolin-2-yl)-p-toluate and methyl 6-(4-isopropyl-4-methyl-5-oxo-2-imidazolin-2-yl)-m-toluate or 2-(4-isopropyl-4-methyl-5-oxo-2-imidazolin-2-yl)-5-methylniconitic acid, especially 5-ethyl-2-(4-isopropyl-4-methyl-5-oxo-2-imidazolin-2-yl)nicotinic acid or 2-(4-isopropyl-4-methyl-5-oxo-2-imidazolin-2-yl)-5-methylnicotinic acid.

In a second preferred method of the present invention, wheat, barley and sorghum plants are safened from injury caused by a herbicidally effective amount of an imidazolinone compound, a dinitroaniline compound, a sulfonylurea compound, a sulfamoylurea compound, an oxime compound, a 2-(4-aryloxyphenoxy)propionic acid compound, a 2-chloroacetanilide compound or an isoxazolyl-2-imidazolidinone compound by applying to the seed of the wheat, barley or sorghum plant an effective antidotal amount of a safener compound of formula I.

The method of the present invention is particularly useful for safening wheat from injury caused by a herbicidally effective amount of a dinitroaniline compound, especially N-(1-ethylpropyl)-2,6-dinitro-3,4-xylidine, by applying to the seed of the wheat an effective antidotal amount of a safener compound of formula I.

In a third preferred method of the present invention, wheat, barley and sorghum plants are safened from injury caused by a herbicidally effective amount of an imidazolinone compound, a sulfonylurea compound, a sulfamoylurea compound, an oxime compound, a 2-(4-aryloxyphenoxy)propionic acid compound or an isoxazolyl-2-imidazolidinone compound by applying to the wheat, barley or sorghum plant an effective antidotal amount of a safener compound of formula I.

The method of the present invention is particularly useful for safening wheat from injury caused by a herbicidally effective amount of an imidazolinone compound, a sulfamoylurea compound, a 2-(4-aryloxyphenoxy)propionic acid compound or an isoxazolyl-2-imidazolidinone compound by applying to the wheat plant an effective antidotal amount of a safener compound of formula I.

In a fourth preferred method of the present invention, rice and oat plants are safened from injury caused by a herbicidally effective amount of an imidazolinone compound, a sulfonylurea compound, a sulfamoylurea compound, an oxime compound, a 2-(4-aryloxyphenoxy)propionic acid compound or an isoxazolyl-2-imidazolidinone compound by applying to the rice or oat plant or seed of the rice or oat plant an effective antidotal amount of a safener compound of formula I.

The method of the present invention is particularly useful for safening rice from injury caused by a herbicidally effective amount of an imidazolinone compound, a sulfonylurea compound, a sulfamoylurea compound, an oxime compound or a 2-(4-aryloxy-phenoxy)propionic acid compound.

The present invention also provides a safener composition comprising an agronomically acceptable inert solid or liquid carrier and about 0.5 to 95% by weight of a safener compound of formula I.

The present invention further provides novel compounds having the structural formula

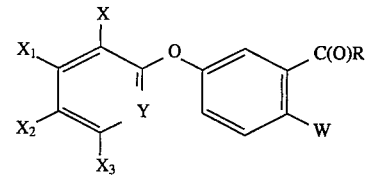

wherein

Y is N or $CX_4$;

X, $X_1$, $X_2$, $X_3$ and $X_4$ are each independently hydrogen, halogen, $C_1$–$C_4$alkyl, $C_1$–$C_4$haloalkyl, $C_1$–$C_4$alkoxy or $C_1$–$C_4$haloalkoxy;

W is $O(CR_1R_2)_nC(O)R_3$, $CR_4$=$CR_5C(O)R_6$ or

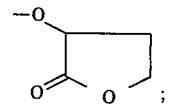

R, $R_3$ and $R_6$ are each independently $OR_7$ or $R_8$;

$R_7$ is hydrogen, $C_1$–$C_4$alkyl, $C_2$–$C_6$alkenyl, $C_2$–$C_6$alkynyl, furfuryl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_8$ is hydrogen, $C_1$–$C_4$alkyl, $C_2$–$C_6$alkenyl, $C_2$–$C_6$alkynyl, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_1$ is hydrogen, halogen, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $C_1$–$C_{12}$alkyl optionally substituted with phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_2$, $R_4$ and $R_5$ are each independently hydrogen, halogen or $C_1$–$C_4$alkyl;

n is an integer of 1, 2, 3 or 4; or when $R_1$ and $R_2$ are not the same, the optical isomers thereof;

provided that when $R_1$ is hydrogen or $C_1$–$C_6$alkyl, $R_2$ is hydrogen or $C_1$–$C_4$alkyl and $R_3$ is $O(C_1$–$C_4$alkyl), then R is other than $O(C_1$–$C_4$alkyl).

It has been found that the safener compounds of this invention do not protect weeds from herbicidal injury. In fact, excellent weed control is maintained in the presence of the safener compounds of the present invention.

Safening of cereal crops such as corn, wheat, sorghum, oat, barley and rice from the postemergence application of herbicides may be effected by allowing the crop plants to grow until the third to fourth leaf stage then spraying with an aqueous solution of the safener either alone or tank mixed with at least one of the above described herbicides. If the herbicide is applied before the safener, the safener should be applied prior to significant crop injury. The tank mix should contain an effective amount of herbicide and an effective amount of safener. Although rates will naturally vary with the particular herbicide and crop, typical rates of application for the safener are about 0.032 kg/ha to 2.0 kg/ha, preferably about 0.10 kg/ha to 1.0 kg/ha.

The present invention may also be practiced by applying the herbicide and/or safener to the soil pre-emergence. A tank mix of the safener and herbicide may be conveniently prepared and employed or sequential spraying may be used in accordance with the present method.

A wide variety of troublesome weed species can also be effectively controlled in the presence of important agronomic cereal crops such as corn, wheat, sorghum, oat, barley and rice by safening the crop plants by uniformly coating the crop seeds with a 5% to 50% composition of the safener, preferably a wettable powder composition, planting the coated seed in the usual manner, and spraying the soil with a herbicide or by incorporating the herbicide into the soil before the coated seeds have been planted or by allowing the crop plants from the coated seeds to grow until the third to fourth leaf stage then spraying with a herbicide. Although rates will vary with the particular herbicide and crop, typical rates of application are about 0.10 mg to 4.0 mg of safener per gram of crop seed, preferably about 0.50 mg to 4.0 mg of safener per gram of crop seed.

In order to facilitate a further understanding of the invention, the following examples are presented primarily for the purpose of illustrating more specific details thereof. The invention is not be deemed limited thereby except as defined in the claims.

EXAMPLE 1

Evaluation of α-Carboxy-5-[(2-chloro-α,α,α-trifluoro-p-tolyl)oxy]-o-anisic acid, dimethyl ester as a safener for corn injury from postemergence application of herbicides Corn plants (Pioneer 3475) in the third leaf stage are sprayed with a formulation of the appropriate herbicide, or a formulation of the appropriate herbicide mixed with a formulation of α-carboxy-5-[(2-chloro -α,α,α-trifluoro-p-tolyl)oxy]-o-anisic acid, dimethyl ester. The herbicide and safener are diluted with water to provide the equivalent of 0.0015 kg/ha to 1.0 kg/ha of herbicide and 0.50 kg/ha of safener to the foliage when applied through a spray nozzle operating as 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2–4 weeks after treatment, the tests are terminated and each pot is examined and rated by measuring the height of the foliage. The test results are averaged and expressed as a percent growth reduction compared to an untreated check, using the following formula:

$$\% \text{ Growth Reduction} = 100 - \left[ \frac{\text{Height of Treated Plants}}{\text{Height of Untreated Plants}} \times 100 \right]$$

The results are summarized in Table I wherein

A is α-carboxy-5-[(2-chloro-α,α,α-trifluoro-p-tolyl)oxy]-o-anisic acid, dimethyl ester;

B is 5-ethyl-2-(4-isopropyl-4-methyl-5-oxo-2-imidazolin-2-yl)nicotinic acid;

C is isopropylammonium 2-(4-isopropyl-4-methyl-5-oxo-2-imidazolin-2-yl)nicotinate;

D is 2-(4-isopropyl-4-methyl-5-oxo-2-imidazolin-2-yl)-3-quinolinecarboxylic acid;

E is 2-(4-isopropyl-4-methyl-5-oxo-2-imidazolin-2-yl)-5-methylnicotinic acid;

F is 2-(4-isopropyl-4-methyl-5-oxo-2-imidazolin-2-yl)-5-(methoxymethyl)nicotinic acid;

G is methyl 2-(4-isopropyl-4-methyl-5-oxo -2-imidazolin-2-yl)nicotinate;

H is methyl o-{{3-[4,6-bis(difluoromethoxy)-2-pyrimidinyl]ureido}sulfonyl}benzoate;

I is 1-[(o-chlorophenyl)sulfonyl]-3-(4-methoxy-6-methyl-s-triazin-2-yl)urea;

J is ethyl o-{[(4-chloro-6-methoxy-2-pyrimidinyl)carbamoyl]sulfamoyl}benzoate;

K is 1-[(o-acetylphenyl)sulfamoyl]-3-(4-methoxy-6-methyl-2-pyrimidinyl)urea;

L is 1-[(o-acetylphenyl)sulfamoyl]-3-(4,6-dimethoxy-2-pyrimidinyl)urea;

M is 1-{[o-(cyclopropylcarbonyl)phenyl]sulfamoyl}-3-(4,6-dimethoxy-2-pyrimidinyl)urea;

N is 3-{p-[(3,5-dichloro-2-pyridyl)oxy]phenoxy}-2-hydroxy-butyronitrile ethyl carbonate;

O is methyl 2-{p-{[3-chloro-5-(trifluoromethyl)-2-pyridyl]oxy}phenoxy}propionate;

P is ethyl 2-{p-[(6-chloro-2-benzoxazolyl)oxy]phenoxy}propionate;

Q is the 2-(O-ethyloxime) of 2-butyryl-5-[2-(ethylthio)propyl]-3-hydroxy-2-cyclohexen-1-one;

R is 3-(5-tert-butyl-3-isoxazolyl)-4-hydroxy-1-methyl-2-imidazolidinone; and

S is 3-(3,4-dichlorophenyl)-1,1-dimethylurea.

TABLE I

| Treatment | Rate (kg/ha) | % Growth Reduction |
| --- | --- | --- |
| B | 0.05 | 32 |
| B + A | 0.05 + 0.50 | 7 |
| B | 0.10 | 57 |
| B + A | 0.10 + 0.50 | 22 |
| C | 0.012 | 49 |
| C + A | 0.012 + 0.50 | 76 |
| C | 0.025 | 49 |
| C + A | 0.025 + 0.50 | 75 |
| D | 0.012 | 80 |
| D + A | 0.012 + 0.50 | 28 |
| D | 0.025 | 87 |
| D + A | 0.025 + 0.50 | 38 |
| E | 0.05 | 28 |
| E + A | 0.05 + 0.50 | 3 |
| E | 0.075 | 71 |
| E + A | 0.075 + 0.50 | 10 |

TABLE I-continued

| Treatment | Rate (kg/ha) | % Growth Reduction |
|---|---|---|
| F | 0.025 | 71 |
| F + A | 0.025 + 0.50 | 30 |
| G | 0.012 | 5 |
| G + A | 0.012 + 0.50 | 18 |
| G | 0.025 | 46 |
| G + A | 0.025 + 0.50 | 31 |
| H | 0.075 | 23 |
| H + A | 0.075 + 0.50 | 14 |
| H | 0.10 | 29 |
| H + A | 0.10 + 0.50 | 7 |
| I | 0.0015 | 72 |
| I + A | 0.0015 + 0.50 | 39 |
| I | 0.003 | 75 |
| I + A | 0.003 + 0.50 | 51 |
| J | 0.025 | 46 |
| J + A | 0.025 + 0.50 | 23 |
| J | 0.05 | 53 |
| J + A | 0.05 + 0.50 | 35 |
| K | 0.003 | 68 |
| K + A | 0.003 + 0.50 | 60 |
| K | 0.006 | 71 |
| K + A | 0.006 + 0.50 | 73 |
| L | 0.012 | 6 |
| L + A | 0.012 + 0.50 | 7 |
| L | 0.025 | 39 |
| L + A | 0.025 + 0.50 | 15 |
| M | 0.012 | 0 |
| M + A | 0.012 + 0.50 | −4 |
| M | 0.025 | 15 |
| M + A | 0.025 + 0.50 | −2 |
| N | 0.25 | 74 |
| N + A | 0.25 + 0.50 | 73 |
| O | 0.012 | 72 |
| O + A | 0.012 + 0.50 | 69 |
| O | 0.025 | 68 |
| O + A | 0.025 + 0.50 | 70 |
| P | 0.006 | 68 |
| P + A | 0.006 + 0.50 | 27 |
| P | 0.012 | 75 |
| P + A | 0.012 + 0.50 | 77 |
| Q | 0.025 | 38 |
| Q + A | 0.025 + 0.50 | 11 |
| Q | 0.05 | 68 |
| Q + A | 0.05 + 0.50 | 26 |
| R | 0.05 | 19 |
| R + A | 0.05 + 0.50 | 19 |
| R | 0.10 | 58 |
| R + A | 0.10 + 0.50 | 38 |
| S | 0.50 | 5 |
| S + A | 0.50 + 0.50 | 10 |
| S | 1.0 | 21 |
| S + A | 1.0 + 0.50 | 16 |

EXAMPLE 2

Evaluation of α-Carboxy-5-[(2-chloro-α,α,α-trifluoro-p-tolyl)oxy]-o-anisic acid, dimethyl ester as a safener for sorghum injury from postemergence application of herbicides Sorghum plants (NC 271) approximately 4 to 5 inches tall are sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 0.0015 kg/ha to 1.0 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table II wherein A–S are as described in Example 1.

TABLE II

| Treatment | Rate (kg/ha) | % Growth Reduction |
|---|---|---|
| B | 0.003 | −3 |
| B + A | 0.003 + 0.50 | −3 |
| B | 0.006 | −7 |
| B + A | 0.006 + 0.50 | 1 |
| C | 0.012 | 12 |
| C + A | 0.012 + 0.50 | 11 |
| C | 0.025 | 77 |
| C + A | 0.025 + 0.50 | 75 |
| D | 0.012 | 38 |
| D + A | 0.012 + 0.50 | 11 |
| D | 0.025 | 41 |
| D + A | 0.025 + 0.50 | 23 |
| E | 0.025 | 75 |
| E + A | 0.025 + 0.50 | 79 |
| E | 0.05 | 78 |
| E + A | 0.05 + 0.50 | 82 |
| F | 0.025 | 71 |
| F + A | 0.025 + 0.50 | 38 |
| G | 0.012 | 0 |
| G + A | 0.012 + 0.50 | 3 |
| G | 0.025 | 15 |
| G + A | 0.025 + 0.50 | 4 |
| H | 0.0015 | 17 |
| H + A | 0.0015 + 0.50 | 17 |
| H | 0.003 | 38 |
| H + A | 0.003 + 0.50 | 30 |
| I | 0.0015 | 46 |
| I + A | 0.0015 + 0.50 | 22 |
| I | 0.003 | 60 |
| I + A | 0.003 + 0.50 | 29 |
| J | 0.025 | 78 |
| J + A | 0.025 + 0.50 | 61 |
| J | 0.05 | 78 |
| J + A | 0.05 + 0.50 | 76 |
| K | 0.006 | 31 |
| K + A | 0.006 + 0.50 | 26 |
| K | 0.012 | 36 |
| K + A | 0.012 + 0.50 | 22 |
| L | 0.012 | −5 |
| L + A | 0.012 + 0.50 | 13 |
| L | 0.025 | −8 |
| L + A | 0.025 + 0.50 | −3 |
| M | 0.012 | 14 |
| M + A | 0.012 + 0.50 | 7 |
| M | 0.025 | 29 |
| M + A | 0.025 + 0.50 | 11 |
| N | 0.25 | 75 |
| N + A | 0.25 + 0.50 | 73 |
| O | 0.012 | 75 |
| O + A | 0.012 + 0.50 | 78 |
| O | 0.025 | 77 |
| O + A | 0.025 + 0.50 | 76 |
| P | 0.006 | 63 |
| P + A | 0.006 + 0.50 | 37 |
| P | 0.012 | 54 |
| P + A | 0.012 + 0.50 | 63 |
| Q | 0.025 | 13 |
| Q + A | 0.025 + 0.50 | 13 |
| Q | 0.05 | 54 |
| Q + A | 0.05 + 0.50 | 14 |
| R | 0.05 | 9 |
| R + A | 0.05 + 0.50 | −11 |
| R | 0.10 | 15 |
| R + A | 0.10 + 0.50 | 17 |

TABLE II-continued

| Treatment | Rate (kg/ha) | % Growth Reduction |
|---|---|---|
| S | 0.50 | 23 |
| S + A | 0.50 + 0.50 | 19 |
| S | 1.0 | 21 |
| S + A | 1.0 + 0.50 | 28 |

EXAMPLE 3

Evaluation of α-Carboxy-5-[(2-chloro-α,α,
α-trifluoro-p-tolyl)oxy]-o-anisic acid, dimethyl ester
as a safener for oat injury from postemergence
application of herbicides Oat plants (Porter) approximately 4 to 5 inches tall are sprayed with a formulation of the appropriate herbicide, or a formulation of the appropriate herbicide mixed with a formulation of α-carboxy-5-[(2-chloro -α,α,α-trifluoro-p-tolyl)oxy]-o-anisic acid, dimethyl ester. The herbicide and safener are diluted with water to provide the equivalent of 0.012 kg/ha to 1.0 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table III wherein A-S are as described in Example 1.

TABLE III

| Treatment | Rate (kg/ha) | % Growth Reduction |
|---|---|---|
| B | 0.012 | 21 |
| B + A | 0.012 + 0.50 | 17 |
| B | 0.025 | 68 |
| B + A | 0.025 + 0.50 | 51 |
| C | 0.012 | 66 |
| C + A | 0.012 + 0.50 | 36 |
| C | 0.025 | 71 |
| C + A | 0.025 + 0.50 | 67 |
| D | 0.012 | 35 |
| D + A | 0.012 + 0.50 | -2 |
| D | 0.025 | 78 |
| D + A | 0.025 + 0.50 | 18 |
| E | 0.05 | 73 |
| E + A | 0.05 + 0.50 | 74 |
| E | 0.10 | 75 |
| E + A | 0.10 + 0.50 | 76 |
| F | 0.05 | 70 |
| F + A | 0.05 + 0.50 | 70 |
| G | 0.025 | 30 |
| G + A | 0.025 + 0.50 | 41 |
| G | 0.05 | 61 |
| G + A | 0.05 + 0.50 | 56 |
| H | 0.075 | 77 |
| H + A | 0.075 + 0.50 | 73 |
| H | 0.10 | 73 |
| H + A | 0.10 + 0.50 | 75 |
| I | 0.10 | 46 |
| I + A | 0.10 + 0.50 | 36 |
| J | 0.025 | 68 |

TABLE III-continued

| Treatment | Rate (kg/ha) | % Growth Reduction |
|---|---|---|
| J + A | 0.025 + 0.50 | 71 |
| J | 0.05 | 72 |
| J + A | 0.05 + 0.50 | 72 |
| K | 0.025 | 63 |
| K + A | 0.025 + 0.50 | 50 |
| K | 0.05 | 59 |
| K + A | 0.05 + 0.50 | 60 |
| L | 0.25 | 37 |
| L + A | 0.25 + 0.50 | 23 |
| L | 0.50 | 47 |
| L + A | 0.50 + 0.50 | 40 |
| M | 0.012 | 13 |
| M + A | 0.012 + 0.50 | 14 |
| M | 0.025 | 20 |
| M + A | 0.025 + 0.50 | 11 |
| N | 0.25 | -18 |
| N + A | 0.25 + 0.50 | -16 |
| N | 0.50 | 2 |
| N + A | 0.50 + 0.50 | -10 |
| O | 0.012 | -9 |
| O + A | 0.012 + 0.50 | -5 |
| O | 0.025 | 10 |
| O + A | 0.025 + 0.50 | 1 |
| P | 0.025 | 5 |
| P + A | 0.025 + 0.50 | -2 |
| P | 0.05 | 3 |
| P + A | 0.05 + 0.50 | 4 |
| Q | 0.10 | 19 |
| Q + A | 0.10 + 0.50 | 29 |
| Q | 0.25 | 72 |
| Q + A | 0.25 + 0.50 | 72 |
| R | 0.05 | 9 |
| R + A | 0.05 + 0.50 | 13 |
| R | 0.10 | 40 |
| R + A | 0.10 + 0.50 | 26 |
| S | 0.50 | 11 |
| S + A | 0.50 + 0.50 | 24 |
| S | 1.0 | 15 |
| S + A | 1.0 + 0.50 | 19 |

EXAMPLE 4

Evaluation of α-Carboxy-5-[(2-chloro-α,α,
α-trifluoro-p-tolyl)oxy]-o-anisic acid, dimethyl ester
as a safener for rice injury from postemergence
application of herbicides Rice plants (Tebonnet) approximately 4 to 5 inches tall are sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 0.0015 kg/ha to 1.0 kg/ha of herbicide and 0.50 kg/ha of safener to the foliage when applied through a spray nozzle operating at psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table IV wherein A–S are as described in Example 1.

TABLE IV

| Treatment | Rate (kg/ha) | % Growth Reduction |
|---|---|---|
| B | 0.003 | 3 |
| B + A | 0.003 + 0.50 | −7 |
| B | 0.006 | 17 |
| B + A | 0.006 + 0.50 | 8 |
| C | 0.012 | 60 |
| C + A | 0.012 + 0.50 | 54 |
| C | 0.025 | 66 |
| C + A | 0.025 + 0.50 | 68 |
| D | 0.012 | 22 |
| D + A | 0.012 + 0.50 | 22 |
| D | 0.025 | 49 |
| D + A | 0.025 + 0.50 | 35 |
| E | 0.025 | 64 |
| E + A | 0.025 + 0.50 | 65 |
| E | 0.05 | 72 |
| E + A | 0.05 + 0.50 | 84 |
| F | 0.025 | 70 |
| F + A | 0.025 + 0.50 | 74 |
| G | 0.012 | 6 |
| G + A | 0.012 + 0.50 | 21 |
| G | 0.025 | 36 |
| G + A | 0.025 + 0.50 | 29 |
| H | 0.0015 | 33 |
| H + A | 0.0015 + 0.50 | 24 |
| H | 0.003 | 65 |
| H + A | 0.003 + 0.50 | 46 |
| I | 0.0015 | 61 |
| I + A | 0.0015 + 0.50 | 56 |
| I | 0.003 | 60 |
| I + A | 0.003 + 0.50 | 66 |
| J | 0.025 | 66 |
| J + A | 0.025 + 0.50 | 60 |
| J | 0.05 | 63 |
| J + A | 0.05 + 0.50 | 64 |
| K | 0.05 | 40 |
| K + A | 0.05 + 0.50 | 47 |
| K | 0.10 | 49 |
| K + A | 0.10 + 0.50 | 40 |
| L | 0.012 | −2 |
| L + A | 0.012 + 0.50 | −12 |
| L | 0.025 | −1 |
| L + A | 0.025 + 0.50 | 8 |
| M | 0.012 | 20 |
| M + A | 0.012 + 0.50 | 8 |
| M | 0.025 | 7 |
| M + A | 0.025 + 0.50 | 1 |
| N | 0.25 | 8 |
| N + A | 0.25 + 0.50 | 7 |
| O | 0.012 | 10 |
| O + A | 0.012 + 0.50 | 5 |
| O | 0.025 | 5 |
| O + A | 0.025 + 0.50 | 33 |
| P | 0.006 | 19 |
| P + A | 0.006 + 0.50 | 10 |
| P | 0.012 | 22 |
| P + A | 0.012 + 0.50 | 16 |
| Q | 0.025 | 12 |
| Q + A | 0.025 + 0.50 | 18 |
| Q | 0.05 | 41 |
| Q + A | 0.05 + 0.50 | 11 |
| R | 0.05 | 50 |
| R + A | 0.05 + 0.50 | 50 |
| R | 0.10 | 49 |
| R + A | 0.10 + 0.50 | 51 |
| S | 0.50 | −3 |
| S + A | 0.50 + 0.50 | 6 |
| S | 1.0 | 7 |
| S + A | 1.0 + 0.50 | −1 |

EXAMPLE 5

Evaluation of α-Carboxy-5-[(2-chloro-α,α,α-trifluoro-p-tolyl)oxy]-o-anisic acid, dimethyl ester as a safener for spring barley injury from postemergence application of herbicides Spring barley plants (Volga) approximately 4 to 5 inches tall are sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 0.012 kg/ha to 1.0 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table V wherein A–S are as described in Example 1.

TABLE V

| Treatment | Rate (kg/ha) | % Growth Reduction |
|---|---|---|
| B | 0.05 | 22 |
| B + A | 0.05 + 0.50 | 5 |
| B | 0.10 | 43 |
| B + A | 0.10 + 0.50 | 35 |
| C | 0.012 | 44 |
| C + A | 0.012 + 0.50 | 43 |
| C | 0.025 | 59 |
| C + A | 0.025 + 0.50 | 57 |
| D | 0.012 | 32 |
| D + A | 0.012 + 0.50 | 15 |
| D | 0.025 | 37 |
| D + A | 0.025 + 0.50 | 34 |
| E | 0.05 | 65 |
| E + A | 0.05 + 0.50 | 63 |
| E | 0.075 | 68 |
| E + A | 0.075 + 0.50 | 66 |
| F | 0.025 | 42 |
| F + A | 0.025 + 0.50 | 44 |
| G | 0.025 | 31 |
| G + A | 0.025 + 0.50 | 32 |
| G | 0.05 | 29 |
| G + A | 0.05 + 0.50 | 37 |
| H | 0.075 | 69 |
| H + A | 0.075 + 0.50 | 72 |
| H | 0.10 | 71 |
| H + A | 0.10 + 0.50 | 69 |
| I | 0.10 | 45 |
| I + A | 0.10 + 0.50 | 50 |
| J | 0.025 | 56 |
| J + A | 0.025 + 0.50 | 58 |
| J | 0.05 | 67 |
| J + A | 0.05 + 0.50 | 63 |
| K | 0.025 | 55 |
| K + A | 0.025 + 0.50 | 51 |
| K | 0.05 | 56 |
| K + A | 0.05 + 0.50 | 60 |
| L | 0.25 | 12 |
| L + A | 0.25 + 0.50 | 15 |
| L | 0.50 | 29 |
| L + A | 0.50 + 0.50 | 23 |
| M | 0.012 | −7 |

TABLE V-continued

| Treatment | Rate (kg/ha) | % Growth Reduction |
|---|---|---|
| M + A | 0.012 + 0.50 | −8 |
| M | 0.025 | 1 |
| M + A | 0.025 + 0.50 | −2 |
| N | 0.25 | −1 |
| N + A | 0.25 + 0.50 | −6 |
| N | 0.50 | −8 |
| N + A | 0.50 + 0.50 | −13 |
| O | 0.012 | 7 |
| O + A | 0.012 + 0.50 | −2 |
| O | 0.025 | 6 |
| O + A | 0.025 + 0.50 | 15 |
| P | 0.025 | 26 |
| P + A | 0.025 + 0.50 | 6 |
| P | 0.05 | 24 |
| P + A | 0.05 + 0.50 | 3 |
| Q | 0.10 | 13 |
| Q + A | 0.10 + 0.50 | 15 |
| Q | 0.25 | 30 |
| Q + A | 0.25 + 0.50 | 24 |
| R | 0.05 | 11 |
| R + A | 0.05 + 0.50 | 11 |
| R | 0.10 | 19 |
| R + A | 0.10 + 0.50 | 27 |
| S | 0.50 | 8 |
| S + A | 0.50 + 0.50 | 22 |
| S | 1.0 | 21 |
| S + A | 1.0 + 0.50 | 18 |

EXAMPLE 6

Evaluation of α-Carboxy-5-[(2-chloro-α,α,α-trifluoro-p-tolyl)oxy]-o-anisic acid, dimethyl ester as a safener for winter barley injury postemergence application of herbicides Winter barley plants (Marinka) approximately 4 to 5 inches tall are sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 0.012 kg/ha to 1.0 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table VI wherein A–S are as described in Example 1.

TABLE VI

| Treatment | Rate (kg/ha) | % Growth Reduction |
|---|---|---|
| B | 0.05 | 32 |
| B + A | 0.05 + 0.50 | 4 |
| B | 0.10 | 55 |
| B + A | 0.10 + 0.50 | 42 |
| C | 0.012 | 34 |
| C + A | 0.012 + 0.50 | 30 |
| C | 0.025 | 59 |
| C + A | 0.025 + 0.50 | 57 |
| D | 0.012 | 34 |
| D + A | 0.012 + 0.50 | 22 |
| D | 0.025 | 46 |
| D + A | 0.025 + 0.50 | 50 |
| E | 0.05 | 61 |
| E + A | 0.05 + 0.50 | 59 |
| E | 0.075 | 61 |
| E + A | 0.075 + 0.50 | 63 |
| F | 0.025 | 41 |
| F + A | 0.025 + 0.50 | 49 |
| G | 0.025 | 21 |
| G + A | 0.025 + 0.50 | 31 |
| G | 0.05 | 33 |
| G + A | 0.05 + 0.50 | 50 |
| H | 0.075 | 60 |
| H + A | 0.075 + 0.50 | 65 |
| H | 0.10 | 64 |
| H + A | 0.10 + 0.50 | 66 |
| I | 0.10 | 36 |
| I + A | 0.10 + 0.50 | 23 |
| J | 0.025 | 53 |
| J + A | 0.025 + 0.50 | 58 |
| J | 0.05 | 64 |
| J + A | 0.05 + 0.50 | 62 |
| K | 0.025 | 60 |
| K + A | 0.025 + 0.50 | 47 |
| K | 0.05 | 61 |
| K + A | 0.05 + 0.50 | 60 |
| L | 0.25 | 27 |
| L + A | 0.25 + 0.50 | 29 |
| L | 0.50 | 42 |
| L + A | 0.50 + 0.50 | 37 |
| M | 0.012 | 13 |
| M + A | 0.012 + 0.50 | 8 |
| M | 0.025 | 14 |
| M + A | 0.025 + 0.50 | 6 |
| N | 0.25 | −11 |
| N + A | 0.25 + 0.50 | −12 |
| N | 0.50 | −15 |
| N + A | 0.50 + 0.50 | −9 |
| O | 0.012 | 15 |
| O + A | 0.012 + 0.50 | −4 |
| O | 0.025 | 36 |
| O + A | 0.025 + 0.50 | 8 |
| P | 0.025 | 4 |
| P + A | 0.025 + 0.50 | 13 |
| P | 0.05 | 16 |
| P + A | 0.05 + 0.50 | 8 |
| Q | 0.10 | 12 |
| Q + A | 0.10 + 0.50 | 8 |
| Q | 0.25 | 36 |
| Q + A | 0.25 + 0.50 | 23 |
| R | 0.05 | 5 |
| R + A | 0.05 + 0.50 | 3 |
| R | 0.10 | 18 |
| R + A | 0.10 + 0.50 | 11 |
| S | 0.50 | 9 |
| S + A | 0.50 + 0.50 | 13 |
| S | 1.0 | 4 |
| S + A | 1.0 + 0.50 | 10 |

EXAMPLE 7

Evaluation of α-Carboxy-5-[(2-chloro-α,α,α-trifluoro-p-tolyl)oxy]-o-anisic acid, dimethyl ester as a safener for durum (spring) wheat injury from postemergence application of herbicides Durum (spring) wheat plants (Wakooma) approximately 4 to 5 inches tall are sprayed with a formulation of the appropriate herbicide, or a formulation of the appropriate herbicide mixed with a formulation of α-carboxy-5-[(2- chloro-α,α,α-trifluoro-p-tolyl)oxy]-o-anisic acid, dimethyl ester. The herbicide and safener are diluted with water to provide the equivalent of 0.003 kg/ha to 0.50 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table VII wherein A–S are as described in Example 1.

TABLE VII

| Treatment | Rate (kg/ha) | % Growth Reduction |
| --- | --- | --- |
| B | 0.003 | 7 |
| B + A | 0.003 + 0.50 | 12 |
| B | 0.006 | 15 |
| B + A | 0.006 + 0.50 | 14 |
| C | 0.012 | 35 |
| C + A | 0.012 + 0.50 | 23 |
| C | 0.025 | 55 |
| C + A | 0.025 + 0.50 | 39 |
| D | 0.012 | 9 |
| D + A | 0.012 + 0.50 | 2 |
| D | 0.025 | 13 |
| D + A | 0.025 + 0.50 | 13 |
| E | 0.05 | 67 |
| E + A | 0.05 + 0.50 | 64 |
| E | 0.10 | 67 |
| E + A | 0.10 + 0.50 | 71 |
| F | 0.025 | 53 |
| F + A | 0.025 + 0.50 | 51 |
| G | 0.025 | 35 |
| G + A | 0.025 + 0.50 | 72 |
| G | 0.05 | 66 |
| G + A | 0.05 + 0.50 | 52 |
| H | 0.075 | 65 |
| H + A | 0.075 + 0.50 | 69 |
| H | 0.10 | 67 |
| H + A | 0.10 + 0.50 | 68 |
| I | 0.10 | 59 |
| I + A | 0.10 + 0.50 | 65 |
| J | 0.025 | 68 |
| J + A | 0.025 + 0.50 | 65 |
| J | 0.05 | 68 |
| J + A | 0.05 + 0.50 | 72 |
| K | 0.025 | 57 |
| K + A | 0.025 + 0.50 | 59 |
| K | 0.05 | 57 |
| K + A | 0.05 + 0.50 | 59 |
| L | 0.25 | 27 |
| L + A | 0.25 + 0.50 | 29 |
| L | 0.50 | 42 |
| L + A | 0.50 + 0.50 | 37 |
| M | 0.012 | -1 |
| M + A | 0.012 + 0.50 | 3 |
| M | 0.025 | 2 |
| M + A | 0.025 + 0.50 | 20 |
| N | 0.25 | 3 |
| N + A | 0.25 + 0.50 | 10 |
| O | 0.012 | 10 |
| O + A | 0.012 + 0.50 | 6 |
| O | 0.025 | 43 |
| O + A | 0.025 + 0.50 | 59 |
| P | 0.025 | 54 |
| P + A | 0.025 + 0.50 | 38 |
| P | 0.05 | 56 |
| P + A | 0.05 + 0.50 | 60 |

TABLE VII-continued

| Treatment | Rate (kg/ha) | % Growth Reduction |
| --- | --- | --- |
| Q | 0.10 | 17 |
| Q + A | 0.10 + 0.50 | 15 |
| Q | 0.25 | 52 |
| Q + A | 0.25 + 0.50 | 54 |
| R | 0.05 | 10 |
| R + A | 0.05 + 0.50 | 2 |
| R | 0.10 | 28 |
| R + A | 0.10 + 0.50 | 11 |
| S | 0.50 | 3 |
| S + A | 0.50 + 0.50 | 6 |
| S | 1.0 | 10 |
| S + A | 1.0 + 0.50 | 8 |

EXAMPLE 8

Evaluation of α-Carboxy-5-[(2-chloro-α,α,α-trifluoro-p-tolyl)oxy]-o-anisic acid, dimethyl ester as a safener for winter wheat injury from postemergence application of herbicides Winter wheat plants (Apollo) approximately 4 to 5 inches tall are sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 0.012 kg/ha to 1.0 kg/ha of herbicide and 0.50 kg/ha of safener to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 2 to 4 weeks after treatment, the tests are terminated and each pot is examined and rated by measuring the height of the foliage. The test results are averaged and expressed as a percent growth reduction compared to an untreated check, as described in Example 1.

The results are summarized in Table VIII wherein A–S are as described in Example 1.

TABLE VIII

| Treatment | Rate (kg/ha) | % Growth Reduction |
| --- | --- | --- |
| B | 0.025 | 11 |
| B + A | 0.025 + 0.50 | 17 |
| B | 0.05 | 32 |
| B + A | 0.05 + 0.50 | 28 |
| C | 0.012 | 31 |
| C + A | 0.012 + 0.50 | 24 |
| C | 0.025 | 57 |
| C + A | 0.025 + 0.50 | 56 |
| D | 0.012 | -2 |
| D + A | 0.012 + 0.50 | 0 |
| D | 0.025 | 2 |
| D + A | 0.025 + 0.50 | 4 |
| E | 0.05 | 21 |
| E + A | 0.05 + 0.50 | 28 |
| E | 0.10 | 53 |
| E + A | 0.10 + 0.50 | 64 |
| F | 0.05 | 44 |
| F + A | 0.05 + 0.50 | 51 |
| G | 0.025 | 15 |
| G + A | 0.025 + 0.50 | 17 |
| G | 0.05 | 30 |

TABLE VIII-continued

| Treatment | Rate (kg/ha) | % Growth Reduction |
|---|---|---|
| G + A | 0.05 + 0.50 | 42 |
| H | 0.075 | 66 |
| H + A | 0.075 + 0.50 | 67 |
| H | 0.10 | 67 |
| H + A | 0.10 + 0.50 | 63 |
| I | 0.10 | 42 |
| I + A | 0.10 + 0.50 | 42 |
| J | 0.025 | 34 |
| J + A | 0.025 + 0.50 | 45 |
| J | 0.05 | 62 |
| J + A | 0.05 + 0.50 | 62 |
| K | 0.025 | 63 |
| K + A | 0.025 + 0.50 | 59 |
| K | 0.05 | 60 |
| K + A | 0.05 + 0.50 | 63 |
| L | 0.25 | 13 |
| L + A | 0.25 + 0.50 | 18 |
| L | 0.50 | 15 |
| L + A | 0.50 + 0.50 | 24 |
| M | 0.012 | −6 |
| M + A | 0.012 + 0.50 | 1 |
| M | 0.025 | −1 |
| M + A | 0.025 + 0.50 | 3 |
| N | 0.25 | −2 |
| N + A | 0.25 + 0.50 | −12 |
| N | 0.50 | −8 |
| N + A | 0.50 + 0.50 | −4 |
| O | 0.012 | 32 |
| O + A | 0.012 + 0.50 | −7 |
| O | 0.025 | 1 |
| O + A | 0.025 + 0.50 | 14 |
| P | 0.025 | 6 |
| P + A | 0.025 + 0.50 | 19 |
| P | 0.05 | 13 |
| P + A | 0.05 + 0.50 | 11 |
| Q | 0.10 | 0 |
| Q + A | 0.10 + 0.50 | 11 |
| Q | 0.25 | 20 |
| Q + A | 0.25 + 0.50 | 23 |
| R | 0.05 | 4 |
| R + A | 0.05 + 0.50 | −1 |
| R | 0.10 | 6 |
| R + A | 0.10 + 0.50 | 8 |
| S | 0.50 | −2 |
| S + A | 0.50 + 0.50 | 14 |
| S | 1.0 | 16 |
| S + A | 1.0 + 0.50 | 19 |

EXAMPLE 9

Evaluation of α-Carboxy-5-[(2-chloro-α,α,α-trifluoro-p-tolyl)oxy]-o-anisic acid, dimethyl ester as a seed treatment for injury to corn caused by postemergence application of herbicides Corn seeds (Pioneer 3475) are treated with the safener α-carboxy-5-[(2-chloro-α,α,α-trifluoro -p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of corn seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 to 3 leaf stage, the corn plants are sprayed with a herbicide solution. The herbicide spray solution is diluted with water to provide the equivalent of 0.0015 kg/ha to 0.25 kg/ha of herbicide to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table IX wherein

A is α-carboxy-5-[(2-chloro-α,α,α-trifluoro-p-tolyl)oxy]-o-anisic acid, dimethyl ester;

B is 5-ethyl-2-(4-isopropyl-4-methyl-5-oxo-2-imidazolin-2-yl)nicotinic acid;

C is isopropylammonium 2-(4-isopropyl-4-methyl-5-oxo-2-imidazolin-2-yl)nicotinate;

D is 2-(4-isopropyl-4-methyl-5-oxo-2-imidazolin-2-yl)-3-quinolinecarboxylic acid;

E is 2-(4-isopropyl-4-methyl-5-oxo-2-imidazolin-2-yl)-5-methylnicotinic acid;

F is 2-(4-isopropyl-4-methyl-5-oxo-2-imidazolin-2-yl)-5-(methoxymethyl)nicotinic acid;

I is 1-[(o-chlorophenyl) sulfonyl]-3-(4-methoxy-6-methyl-s-triazin-2-yl)urea;

L is 1-[(o-acetylphenyl)sulfamoyl]-3-(4,6-dimethoxy-2-pyrimidinyl)urea;

N is 3-{p-[(3,5-dichloro-2-pyridyl)oxy]phenoxy}-2-hydroxy-butyronitrile ethyl carbonate;

O is methyl 2-{p-{[3-chloro-5-(trifluoromethyl)-2-pyridyl]oxy}phenoxy}propionate;

Q is the 2-(O-ethyloxime) of 2-butyryl-5-[2-(ethylthio)propyl]-3-hydroxy-2-cyclohexen-1-one; and R is 3-(5-tert-butyl-3-isoxazolyl)-4-hydroxy-1-methyl-2-imidazolidinone.

TABLE IX

| Treatment | Rate (kg/ha) | Rate (mg/g of seed) | % Growth Reduction |
|---|---|---|---|
| B | 0.05 | | 54 |
| B + A | 0.05 | 0.25 | 26 |
| B + A | 0.05 | 0.50 | 8 |
| B + A | 0.05 | 1.0 | 4 |
| B + A | 0.05 | 2.0 | 2 |
| B + A | 0.05 | 4.0 | −1 |
| B | 0.075 | | 56 |
| B + A | 0.075 | 0.25 | 38 |
| B + A | 0.075 | 0.50 | 24 |
| B + A | 0.075 | 1.0 | 26 |
| B + A | 0.075 | 2.0 | 8 |
| B + A | 0.075 | 4.0 | 10 |
| B | 0.10 | | 58 |
| B + A | 0.10 | 0.25 | 49 |
| B + A | 0.10 | 0.50 | 29 |
| B + A | 0.10 | 1.0 | 32 |
| B + A | 0.10 | 2.0 | 34 |
| B + A | 0.10 | 4.0 | 28 |
| C | 0.006 | | 12 |
| C + A | 0.006 | 0.25 | −3 |
| C + A | 0.006 | 0.50 | 2 |
| C + A | 0.006 | 1.0 | −3 |
| C + A | 0.006 | 2.0 | 0 |
| C + A | 0.006 | 4.0 | 2 |
| C | 0.012 | | 42 |
| C + A | 0.012 | 0.25 | 34 |
| C + A | 0.012 | 0.50 | 42 |

TABLE IX-continued

| Treatment | Rate (kg/ha) | (mg/g of seed) | % Growth Reduction |
| --- | --- | --- | --- |
| C + A | 0.012 | 1.0 | 49 |
| C + A | 0.012 | 2.0 | 50 |
| C + A | 0.012 | 4.0 | 52 |
| C | 0.025 | | 68 |
| C + A | 0.025 | 0.25 | 66 |
| C + A | 0.025 | 0.50 | 63 |
| C + A | 0.025 | 1.0 | 69 |
| C + A | 0.025 | 2.0 | 69 |
| C + A | 0.025 | 4.0 | 76 |
| D | 0.01 | | 57 |
| D + A | 0.01 | 0.25 | 59 |
| D + A | 0.01 | 0.50 | 41 |
| D + A | 0.01 | 1.0 | 38 |
| D + A | 0.01 | 2.0 | 16 |
| D + A | 0.01 | 4.0 | 5 |
| D | 0.025 | | 71 |
| D + A | 0.025 | 0.25 | 63 |
| D + A | 0.025 | 0.50 | 62 |
| D + A | 0.025 | 1.0 | 62 |
| D + A | 0.025 | 2.0 | 64 |
| D + A | 0.025 | 4.0 | 59 |
| E | 0.025 | | 35 |
| E + A | 0.025 | 0.25 | 13 |
| E + A | 0.025 | 0.50 | 10 |
| E + A | 0.025 | 1.0 | 9 |
| E + A | 0.025 | 2.0 | -2 |
| E + A | 0.025 | 4.0 | -1 |
| E | 0.05 | | 64 |
| E + A | 0.05 | 0.25 | 59 |
| E + A | 0.05 | 0.50 | 22 |
| E + A | 0.05 | 1.0 | 11 |
| E + A | 0.05 | 2.0 | 16 |
| E + A | 0.05 | 4.0 | 9 |
| F | 0.012 | | 49 |
| F + A | 0.012 | 0.25 | 15 |
| F + A | 0.012 | 0.50 | 32 |
| F + A | 0.012 | 1.0 | 15 |
| F + A | 0.012 | 2.0 | 23 |
| F + A | 0.012 | 4.0 | 21 |
| F | 0.025 | | 71 |
| F + A | 0.025 | 0.25 | 54 |
| F + A | 0.025 | 0.50 | 63 |
| F + A | 0.025 | 1.0 | 59 |
| F + A | 0.025 | 2.0 | 43 |
| F + A | 0.025 | 4.0 | 47 |
| F | 0.05 | | 73 |
| F + A | 0.05 | 0.25 | 70 |
| F + A | 0.05 | 0.50 | 69 |
| F + A | 0.05 | 1.0 | 66 |
| F + A | 0.05 | 2.0 | 70 |
| F + A | 0.05 | 4.0 | 72 |
| I | 0.0015 | | 31 |
| I + A | 0.0015 | 0.25 | 17 |
| I + A | 0.0015 | 0.50 | 15 |
| I + A | 0.0015 | 1.0 | 14 |
| I + A | 0.0015 | 2.0 | 14 |
| I | 0.003 | | 66 |
| I + A | 0.003 | 0.25 | 37 |
| I + A | 0.003 | 0.50 | 24 |
| I + A | 0.003 | 1.0 | 25 |
| I + A | 0.003 | 2.0 | 27 |
| L | 0.016 | | 34 |
| L + A | 0.016 | 0.25 | 17 |
| L + A | 0.016 | 0.50 | 12 |
| L + A | 0.016 | 1.0 | 14 |
| L + A | 0.016 | 2.0 | 19 |
| L | 0.032 | | 65 |
| L + A | 0.032 | 0.25 | 11 |
| L + A | 0.032 | 0.50 | 17 |
| L + A | 0.032 | 1.0 | 18 |
| L + A | 0.032 | 2.0 | 21 |
| N | 0.10 | | 19 |
| N + A | 0.10 | 0.25 | 9 |
| N + A | 0.10 | 0.50 | 9 |
| N + A | 0.10 | 1.0 | 14 |
| N + A | 0.10 | 2.0 | 27 |
| N | 0.25 | | 71 |
| N + A | 0.25 | 0.25 | 29 |
| N + A | 0.25 | 0.50 | 24 |
| N + A | 0.25 | 1.0 | 22 |
| N + A | 0.25 | 2.0 | 24 |
| O | 0.012 | | 64 |
| O + A | 0.012 | 0.25 | 30 |
| O + A | 0.012 | 0.50 | 14 |
| O + A | 0.012 | 1.0 | 13 |
| O + A | 0.012 | 2.0 | 20 |
| Q | 0.025 | | 74 |
| Q + A | 0.025 | 0.25 | 30 |
| Q + A | 0.025 | 0.50 | 12 |
| Q + A | 0.025 | 1.0 | 7 |
| Q + A | 0.025 | 2.0 | 16 |
| Q | 0.05 | | 74 |
| Q + A | 0.05 | 0.25 | 37 |
| Q + A | 0.05 | 0.50 | 40 |
| Q + A | 0.05 | 1.0 | 34 |
| Q + A | 0.05 | 2.0 | 30 |
| R | 0.125 | | 24 |
| R + A | 0.125 | 0.25 | 25 |
| R + A | 0.125 | 0.50 | 25 |
| R + A | 0.125 | 1.0 | 20 |
| R | 0.25 | | 50 |
| R + A | 0.25 | 0.25 | 40 |
| R + A | 0.25 | 0.50 | 42 |
| R + A | 0.25 | 1.0 | 39 |

EXAMPLE 10

Evaluation of α-Carboxy-5-[(2-chloro-α,α,α-trifluoro-p-tolyl)oxy]-o-anisic acid, dimethyl ester as a seed treatment for injury to barley caused by postemergence application of herbicides Barley seeds (Volga) are treated with the safener α-carboxy-5-[(2-chloro-α,α,α-trifluoro-p-tolyl)-oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of barley seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 1 to 2 leaf stage, the barley plants are sprayed with a herbicide solution. The herbicide spray solution is diluted with water to provide the equivalent of 0.0125 kg/ha to 1.0 kg/ha of herbicide to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table X wherein

A is α-carboxy-5-[(2-chloro-α,α,α-trifluoro-p-tolyl)oxy]-o-anisic acid, dimethyl ester;

B is 5-ethyl-2-(4-isopropyl-4-methyl-5-oxo-2-imidazolin-2-yl)nicotinic acid;

D is 2-(4-isopropyl-4-methyl-5-oxo-2-imidazolin-2-yl)-3-quinolinecarboxylic acid;

H is methyl o-{{3-[4,6-bis(difluoromethoxy)-2-pyrimidinyl]ureido}sulfonyl}benzoate;

I is 1-[(o-chlorophenyl)sulfonyl]-3-(4-methoxy-6-methyl-s-triazin-2-yl)urea;

L is 1-[(o-acetylphenyl)sulfamoyl]-3-(4,6-dimethoxy-2-pyrimidinyl)urea;

N is 3-{p-[(3,5-dichloro-2-pyridyl)oxy]phenoxy}-2-hydroxy-butyronitrile ethyl carbonate;

O is methyl 2-{p-{[3-chloro-5-(trifluoromethyl)-2-pyridyl]oxy}phenoxy}propionate;

P is ethyl 2-{p-[(6-chloro-2-benzoxazolyl) oxy] phenoxy}propionate;

Q is the 2-(O-ethyloxime) of 2-butyryl-5-[2-(ethylthio)propyl]-3-hydroxy-2-cyclohexen-1-one;

R is 3-(5-tert-butyl-3-isoxazolyl)-4-hydroxy-1-methyl-2-imidazolidinone; and

S is 3-(3,4-dichlorophenyl)-1,1-dimethylurea.

TABLE X

| Treatment | Rate (kg/ha) | (mg/g of seed) | % Growth Reduction |
|---|---|---|---|
| B | 0.05 | | 18 |
| B + A | 0.05 | 0.25 | 6 |
| B + A | 0.05 | 0.50 | 0 |
| B + A | 0.05 | 1.0 | 3 |
| B + A | 0.05 | 2.0 | 2 |
| B | 0.075 | | 15 |
| B + A | 0.075 | 0.25 | −5 |
| B + A | 0.075 | 0.50 | −3 |
| B + A | 0.075 | 1.0 | 0 |
| B + A | 0.075 | 2.0 | 6 |
| B + A | 0.075 | 4.0 | 24 |
| B | 0.10 | | 26 |
| B + A | 0.10 | 0.25 | 4 |
| B + A | 0.10 | 0.50 | 31 |
| B + A | 0.10 | 1.0 | 22 |
| B + A | 0.10 | 2.0 | 22 |
| B + A | 0.10 | 4.0 | 30 |
| D | 0.01 | | 8 |
| D + A | 0.01 | 0.25 | 0 |
| D + A | 0.01 | 0.50 | 0 |
| D + A | 0.01 | 1.0 | −5 |
| D + A | 0.01 | 2.0 | −1 |
| D + A | 0.01 | 4.0 | 6 |
| D | 0.025 | | 39 |
| D + A | 0.025 | 0.25 | 29 |
| D + A | 0.025 | 0.50 | 27 |
| D + A | 0.025 | 1.0 | 35 |
| D + A | 0.025 | 2.0 | 60 |
| D + A | 0.025 | 4.0 | 64 |
| H | 0.0125 | | 61 |
| H + A | 0.0125 | 0.25 | 48 |
| H + A | 0.0125 | 0.50 | 47 |
| H + A | 0.0125 | 1.0 | 51 |
| H + A | 0.0125 | 2.0 | 53 |
| H | 0.025 | | 59 |
| H + A | 0.025 | 0.25 | 61 |
| H + A | 0.025 | 0.50 | 61 |
| H + A | 0.025 | 1.0 | 59 |
| H + A | 0.025 | 2.0 | 54 |
| I | 0.05 | | 26 |
| I + A | 0.05 | 0.25 | 9 |
| I + A | 0.05 | 0.50 | 8 |
| I + A | 0.05 | 1.0 | 6 |
| I + A | 0.05 | 2.0 | 7 |
| I | 0.10 | | 40 |
| I + A | 0.10 | 0.25 | 21 |
| I + A | 0.10 | 0.50 | 23 |
| I + A | 0.10 | 1.0 | 22 |
| I + A | 0.10 | 2.0 | 28 |
| L | 0.25 | | 22 |
| L + A | 0.25 | 0.25 | 2 |
| L + A | 0.25 | 0.50 | −2 |
| L + A | 0.25 | 1.0 | 1 |
| L + A | 0.25 | 2.0 | 12 |
| L | 0.50 | | 32 |
| L + A | 0.50 | 0.25 | 8 |
| L + A | 0.50 | 0.50 | 7 |
| L + A | 0.50 | 1.0 | 5 |
| L + A | 0.50 | 2.0 | 5 |
| N | 0.50 | | 19 |
| N + A | 0.50 | 0.25 | −2 |
| N + A | 0.50 | 0.50 | −5 |
| N + A | 0.50 | 1.0 | −2 |
| N + A | 0.50 | 2.0 | 12 |
| N | 1.0 | | 33 |
| N + A | 1.0 | 0.25 | 7 |
| N + A | 1.0 | 0.50 | 23 |
| N + A | 1.0 | 1.0 | 26 |
| N + A | 1.0 | 2.0 | 31 |
| O | 0.02 | | 62 |
| O + A | 0.02 | 0.25 | 66 |
| O + A | 0.02 | 0.50 | 33 |
| O + A | 0.02 | 1.0 | 18 |
| O + A | 0.02 | 2.0 | 14 |
| O | 0.04 | | 75 |
| O + A | 0.04 | 0.25 | 73 |
| O + A | 0.04 | 0.50 | 68 |
| O + A | 0.04 | 1.0 | 65 |
| O + A | 0.04 | 2.0 | 67 |
| P | 0.025 | | −1 |
| P + A | 0.025 | 0.25 | −5 |
| P + A | 0.025 | 0.50 | −6 |
| P + A | 0.025 | 1.0 | −4 |
| P + A | 0.025 | 2.0 | −2 |
| P | 0.05 | | 8 |
| P + A | 0.05 | 0.25 | −6 |
| P + A | 0.05 | 0.50 | −9 |
| P + A | 0.05 | 1.0 | −9 |
| P + A | 0.05 | 2.0 | −7 |
| P | 0.10 | | 20 |
| P + A | 0.10 | 0.25 | −4 |
| P + A | 0.10 | 0.50 | −10 |
| P + A | 0.10 | 1.0 | −11 |
| P + A | 0.10 | 2.0 | −9 |
| Q | 0.10 | | 30 |
| Q + A | 0.10 | 0.25 | 25 |
| Q + A | 0.10 | 0.50 | 25 |
| Q + A | 0.10 | 1.0 | 26 |
| Q + A | 0.10 | 2.0 | 42 |
| Q | 0.20 | | 52 |
| Q + A | 0.20 | 0.25 | 46 |
| Q + A | 0.20 | 0.50 | 46 |
| Q + A | 0.20 | 1.0 | 46 |
| Q + A | 0.20 | 2.0 | 53 |
| R | 0.05 | | 12 |
| R + A | 0.05 | 0.25 | 2 |
| R + A | 0.05 | 0.50 | 6 |
| R + A | 0.05 | 1.0 | 11 |
| R + A | 0.05 | 2.0 | 10 |
| R | 0.10 | | 30 |
| R + A | 0.10 | 0.25 | 21 |
| R + A | 0.10 | 0.50 | 25 |
| R + A | 0.10 | 1.0 | 32 |
| R + A | 0.10 | 2.0 | 36 |
| S | 0.40 | | 23 |

TABLE X-continued

| Treatment | Rate (kg/ha) | (mg/g of seed) | % Growth Reduction |
|---|---|---|---|
| S + A | 0.40 | 0.25 | 20 |
| S + A | 0.40 | 0.50 | 18 |
| S + A | 0.40 | 1.0 | 20 |
| S + A | 0.40 | 2.0 | 29 |
| S | 0.80 |  | 32 |
| S + A | 0.80 | 0.25 | 19 |
| S + A | 0.80 | 0.50 | 18 |
| S + A | 0.80 | 1.0 | 26 |
| S + A | 0.80 | 2.0 | 28 |

EXAMPLE 11

Evaluation of α-Carboxy-5-[(2-chloro-α,α,α-trifluoro-p-tolyl)oxy]-o-anisic acid, dimethyl ester as a seed treatment for injury to oats caused by postemergence application of herbicides Tame oat seeds (Porter) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of oat seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 leaf stage, the oat plants are sprayed with a herbicide solution. The herbicide spray solution is diluted with water to provide the equivalent of 0.025 kg/ha to 0.05 kg/ha of herbicide to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table XI wherein

A is α-carboxy-5-[(2-chloro-α,α,α-trifluoro-p-tolyl)oxy]-o-anisic acid, dimethyl ester;

B is 5-ethyl-2-(4-isopropyl-4-methyl-5-oxo-2-imidazolin-2-yl)nicotinic acid;

D is 2-(4-isopropyl-4-methyl-5-oxo-2-imidazolin-2-yl)-3-quinolinecarboxylic acid;

G is methyl 2-(4-isopropyl-4-methyl-5-oxo -2-imidazolin-2-yl)nicotinate;

I is 1-[(o-chlorophenyl)sulfonyl]-3-(4-methoxy-6-methyl-s-triazin-2-yl)urea;

L is 1-[(o-acetylphenyl)sulfamoyl]-3-(4,6-dimethoxy-2-pyrimidinyl)urea;

N is 3-{p-[(3,5-dichloro-2-pyridyl)oxy]phenoxy}-2-hydroxy-butyronitrile ethyl carbonate;

O is methyl 2-{p-{[3-chloro-5-(trifluoromethyl)-2-pyridyl]oxy}phenoxy}propionate;

Q is the 2-(O-ethyloxime) of 2-butyryl-5-[2-(ethylthio)propyl]-3-hydroxy-2-cyclohexen-1-one;

R is 3-(5-tert-butyl-3-isoxazolyl)-4-hydroxy-1-methyl-2-imidazolidinone; and

S is 3-(3,4-dichlorophenyl)-1,1-dimethylurea.

TABLE XI

| Treatment | Rate (kg/ha) | (mg/g of seed) | % Growth Reduction |
|---|---|---|---|
| B | 0.05 |  | 57 |
| B + A | 0.05 | 0.25 | 60 |
| B + A | 0.05 | 0.50 | 54 |
| B + A | 0.05 | 1.0 | 63 |
| B + A | 0.05 | 2.0 | 64 |
| B + A | 0.05 | 4.0 | 67 |
| B | 0.075 |  | 61 |
| B + A | 0.075 | 0.25 | 52 |
| B + A | 0.075 | 0.50 | 67 |
| B + A | 0.075 | 1.0 | 70 |
| B + A | 0.075 | 2.0 | 62 |
| B + A | 0.075 | 4.0 | 60 |
| B | 0.10 |  | 62 |
| B + A | 0.10 | 0.25 | 59 |
| B + A | 0.10 | 0.50 | 58 |
| B + A | 0.10 | 1.0 | 60 |
| B + A | 0.10 | 2.0 | 64 |
| B + A | 0.10 | 4.0 | 68 |
| D | 0.01 |  | 22 |
| D + A | 0.01 | 0.25 | 13 |
| D + A | 0.01 | 0.50 | 5 |
| D + A | 0.01 | 1.0 | 15 |
| D + A | 0.01 | 2.0 | 18 |
| D + A | 0.01 | 4.0 | 24 |
| D | 0.025 |  | 59 |
| D + A | 0.025 | 0.25 | 56 |
| D + A | 0.025 | 0.50 | 60 |
| D + A | 0.025 | 1.0 | 61 |
| D + A | 0.025 | 2.0 | 71 |
| D + A | 0.025 | 4.0 | 73 |
| G | 0.025 |  | 41 |
| G + A | 0.025 | 0.25 | 24 |
| G + A | 0.025 | 0.50 | 22 |
| G + A | 0.025 | 1.0 | 25 |
| G + A | 0.025 | 2.0 | 22 |
| G + A | 0.025 | 4.0 | 31 |
| G | 0.05 |  | 50 |
| G + A | 0.05 | 0.25 | 49 |
| G + A | 0.05 | 0.50 | 48 |
| G + A | 0.05 | 1.0 | 44 |
| G + A | 0.05 | 2.0 | 52 |
| G + A | 0.05 | 4.0 | 56 |
| I | 0.20 |  | 47 |
| I + A | 0.20 | 0.25 | 35 |
| I + A | 0.20 | 0.50 | 35 |
| I + A | 0.20 | 1.0 | 35 |
| I + A | 0.20 | 2.0 | 29 |
| I | 0.40 |  | 55 |
| I + A | 0.40 | 0.25 | 43 |
| I + A | 0.40 | 0.50 | 40 |
| I + A | 0.40 | 1.0 | 37 |
| I + A | 0.40 | 2.0 | 42 |
| L | 0.25 |  | 42 |
| L + A | 0.25 | 0.25 | 24 |
| L + A | 0.25 | 0.50 | 23 |
| L + A | 0.25 | 1.0 | 22 |
| L + A | 0.25 | 2.0 | 20 |
| L | 0.50 |  | 50 |
| L + A | 0.50 | 0.25 | 44 |
| L + A | 0.50 | 0.50 | 43 |
| L + A | 0.50 | 1.0 | 26 |
| L + A | 0.50 | 2.0 | 28 |
| N | 0.25 |  | 15 |
| N + A | 0.25 | 0.25 | 6 |
| N + A | 0.25 | 0.50 | 0 |
| N + A | 0.25 | 1.0 | 3 |

TABLE XI-continued

| Treatment | Rate (kg/ha) | (mg/g of seed) | % Growth Reduction |
|---|---|---|---|
| N + A | 0.25 | 2.0 | 9 |
| N | 0.50 | | 38 |
| N + A | 0.50 | 0.25 | 26 |
| N + A | 0.50 | 0.50 | 11 |
| N + A | 0.50 | 1.0 | 7 |
| N + A | 0.50 | 2.0 | 16 |
| O | 0.02 | | 47 |
| O + A | 0.02 | 0.25 | 42 |
| O + A | 0.02 | 0.50 | 42 |
| O + A | 0.02 | 1.0 | 39 |
| O + A | 0.02 | 2.0 | 27 |
| O | 0.04 | | 52 |
| O + A | 0.04 | 0.25 | 45 |
| O + A | 0.04 | 0.50 | 45 |
| O + A | 0.04 | 1.0 | 41 |
| O + A | 0.04 | 2.0 | 45 |
| Q | 0.10 | | 48 |
| Q + A | 0.10 | 0.25 | 45 |
| Q + A | 0.10 | 0.50 | 43 |
| Q + A | 0.10 | 1.0 | 43 |
| Q + A | 0.10 | 2.0 | 45 |
| Q | 0.20 | | 53 |
| Q + A | 0.20 | 0.25 | 47 |
| Q + A | 0.20 | 0.50 | 48 |
| Q + A | 0.20 | 1.0 | 45 |
| Q + A | 0.20 | 2.0 | 51 |
| R | 0.05 | | 27 |
| R + A | 0.05 | 0.25 | 15 |
| R + A | 0.05 | 0.50 | 12 |
| R + A | 0.05 | 1.0 | 10 |
| R + A | 0.05 | 2.0 | 14 |
| R | 0.10 | | 47 |
| R + A | 0.10 | 0.25 | 39 |
| R + A | 0.10 | 0.50 | 36 |
| R + A | 0.10 | 1.0 | 28 |
| R + A | 0.10 | 2.0 | 29 |
| S | 0.50 | | 24 |
| S + A | 0.50 | 0.25 | 21 |
| S + A | 0.50 | 0.50 | 18 |
| S + A | 0.50 | 1.0 | 17 |
| S + A | 0.50 | 2.0 | 18 |
| S | 1.0 | | 40 |
| S + A | 1.0 | 0.25 | 24 |
| S + A | 1.0 | 0.50 | 21 |
| S + A | 1.0 | 1.0 | 21 |
| S + A | 1.0 | 2.0 | 27 |

EXAMPLE 12

Evaluation of α-Carboxy-5-[(2-chloro-α,α,α-trifluoro-p-tolyl)oxy]-o-anisic acid, dimethyl ester as a seed treatment for injury to sorghum caused by postemergence application of herbicides Sorghum seeds (NC 271) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of sorghum seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 2 to 3 leaf stage, the sorghum plants are sprayed with a herbicide formulation. The herbicide spray formulation is diluted with water to provide the equivalent of 0.0015 kg/ha to 1.0 kg/ha of herbicide to the foliage when applied through a spray nozzle operating at 40 psi for a predetermined time. The herbicide spray formulation contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table XII wherein

A is α-carboxy-5-[(2-chloro-α,α,α-trifluoro-p-tolyl)oxy]-o-anisic acid, dimethyl ester;

D is 2-(4-isopropyl-4-methyl-5-oxo-2-imidazolin-2-yl)-3-quinolinecarboxylic acid;

H is methyl o-{{3-[4,6-bis(difluoromethoxy)-2-pyrimidinyl]ureido}sulfonyl}benzoate;

I is 1-[(o-chlorophenyl)sulfonyl]-3-(4-methoxy-6-methyl-s-triazin-2-yl)urea;

L is 1-[(o-acetylphenyl) sulfamoyl]-3-(4,6-dimethoxy-2-pyrimidinyl)urea;

N is 3-{p-[(3,5-dichloro-2-pyridyl)oxy]phenoxy}-2-hydroxy-butyronitrile ethyl carbonate;

Q is the 2-(O-ethyloxime) of 2-butyryl-5-[2-(ethylthio)propyl]-3-hydroxy-2-cyclohexen-1-one;

R is 3-(5-tert-butyl-3-isoxazolyl)-4-hydroxy-1-methyl-2-imidazolidinone; and

S is 3-(3,4-dichlorophenyl)-1,1-dimethylurea.

TABLE XII

| Treatment | Rate (kg/ha) | (mg/g of seed) | % Growth Reduction |
|---|---|---|---|
| D | 0.01 | | 17 |
| D + A | 0.01 | 0.25 | −4 |
| D + A | 0.01 | 0.50 | −2 |
| D + A | 0.01 | 1.0 | −3 |
| D + A | 0.01 | 2.0 | −9 |
| D + A | 0.01 | 4.0 | −5 |
| D | 0.025 | | 30 |
| D + A | 0.025 | 0.25 | 39 |
| D + A | 0.025 | 0.50 | 40 |
| D + A | 0.025 | 1.0 | 51 |
| D + A | 0.025 | 2.0 | 40 |
| D + A | 0.025 | 4.0 | 45 |
| H | 0.0015 | | 78 |
| H + A | 0.0015 | 0.25 | 60 |
| H + A | 0.0015 | 0.50 | 53 |
| H + A | 0.0015 | 1.0 | 55 |
| H + A | 0.0015 | 2.0 | 65 |
| H | 0.003 | | 81 |
| H + A | 0.003 | 0.25 | 81 |
| H + A | 0.003 | 0.50 | 81 |
| H + A | 0.003 | 1.0 | 81 |
| H + A | 0.003 | 2.0 | 82 |
| I | 0.0015 | | 33 |
| I + A | 0.0015 | 0.25 | 19 |
| I + A | 0.0015 | 0.50 | 15 |
| I + A | 0.0015 | 1.0 | 13 |
| I + A | 0.0015 | 2.0 | 18 |
| I | 0.003 | | 57 |
| I + A | 0.003 | 0.25 | 33 |
| I + A | 0.003 | 0.50 | 32 |
| I + A | 0.003 | 1.0 | 27 |
| I + A | 0.003 | 2.0 | 27 |
| L | 0.10 | | 55 |
| L + A | 0.10 | 0.25 | 41 |

TABLE XII-continued

| Treatment | Rate (kg/ha) | (mg/g of seed) | % Growth Reduction |
|---|---|---|---|
| L + A | 0.10 | 0.50 | 39 |
| L + A | 0.10 | 1.0 | 40 |
| L + A | 0.10 | 2.0 | 31 |
| L | 0.20 | | 71 |
| L + A | 0.20 | 0.25 | 51 |
| L + A | 0.20 | 0.50 | 55 |
| L + A | 0.20 | 1.0 | 46 |
| L + A | 0.20 | 2.0 | 39 |
| N | 0.10 | | 25 |
| N + A | 0.10 | 0.25 | 9 |
| N + A | 0.10 | 0.50 | 8 |
| N + A | 0.10 | 1.0 | 10 |
| N + A | 0.10 | 2.0 | 8 |
| N | 0.25 | | 61 |
| N + A | 0.25 | 0.25 | 49 |
| N + A | 0.25 | 0.50 | 49 |
| N + A | 0.25 | 1.0 | 43 |
| N + A | 0.25 | 2.0 | 46 |
| Q | 0.025 | | 38 |
| Q + A | 0.025 | 0.25 | 12 |
| Q + A | 0.025 | 0.50 | 16 |
| Q + A | 0.025 | 1.0 | 17 |
| Q + A | 0.025 | 2.0 | 28 |
| Q | 0.05 | | 69 |
| Q + A | 0.05 | 0.25 | 34 |
| Q + A | 0.05 | 0.50 | 45 |
| Q + A | 0.05 | 1.0 | 50 |
| Q + A | 0.05 | 2.0 | 55 |
| R | 0.05 | | 22 |
| R + A | 0.05 | 0.25 | 21 |
| R + A | 0.05 | 0.50 | 15 |
| R + A | 0.05 | 1.0 | 10 |
| R + A | 0.05 | 2.0 | 17 |
| R | 0.10 | | 35 |
| R + A | 0.10 | 0.25 | 34 |
| R + A | 0.10 | 0.50 | 39 |
| R + A | 0.10 | 1.0 | 41 |
| R + A | 0.10 | 2.0 | 44 |
| S | 0.50 | | 21 |
| S + A | 0.50 | 0.25 | 17 |
| S + A | 0.50 | 0.50 | 14 |
| S + A | 0.50 | 1.0 | 24 |
| S + A | 0.50 | 2.0 | 24 |
| S | 1.0 | | 47 |
| S + A | 1.0 | 0.25 | 49 |
| S + A | 1.0 | 0.50 | 49 |
| S + A | 1.0 | 1.0 | 48 |
| S + A | 1.0 | 2.0 | 41 |

EXAMPLE 13

Evaluation of α-Carboxy-5-[(2-chloro-α,α,α-trifluoro-p-tolyl)oxy]-o-anisic acid, dimethyl ester as a seed treatment for injury to wheat caused by postemergence application of herbicides Wheat seeds (APOLLO) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of wheat seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 1 to 2 leaf stage, the wheat plants are sprayed with a herbicide formulation. The herbicide spray formulation is diluted with water to provide the equivalent of 0.02 kg/ha to 1.0 kg/ha of herbicide to the foliage when applied through a spray nozzle operating at 40 psi for a predetermined time. The herbicide spray formulation contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table XIII wherein

A is α-carboxy-5-[(2-chloro-α,α,α-trifluoro-p-tolyl)oxy]-o-anisic acid, dimethyl ester;

I is 1-[(o-chlorophenyl)sulfonyl]-3-(4-methoxy-6-methyl-s-triazin-2-yl)urea;

L is 1-[(o-acetylphenyl)sulfamoyl]-3-(4,6-dimethoxy-2-pyrimidinyl)urea;

O is methyl 2-{p-{[3-chloro-5-(trifluoromethyl)-2-pyridyl]oxy}phenoxy}propionate;

Q is the 2-(O-ethyloxime) of 2-butyryl-5-[2-(ethylthio)propyl]-3-hydroxy-2-cyclohexen-1-one;

R is 3-(5-tert-butyl-3-isoxazolyl)-4-hydroxy-1-methyl-2-imidazolidinone; and

S is 3-(3,4-dichlorophenyl)-1,1-dimethylurea.

TABLE XIII

| Treatment | Rate (kg/ha) | (mg/g of seed) | % Growth Reduction |
|---|---|---|---|
| I | 0.05 | | 12 |
| I + A | 0.05 | 0.25 | −6 |
| I + A | 0.05 | 0.50 | −6 |
| I + A | 0.05 | 1.0 | −3 |
| I + A | 0.05 | 2.0 | 1 |
| I | 0.10 | | 17 |
| I + A | 0.10 | 0.25 | −4 |
| I + A | 0.10 | 0.50 | −1 |
| I + A | 0.10 | 1.0 | 1 |
| I + A | 0.10 | 2.0 | 13 |
| L | 0.50 | | 16 |
| L + A | 0.50 | 0.25 | −3 |
| L + A | 0.50 | 0.50 | −4 |
| L + A | 0.50 | 1.0 | −6 |
| L + A | 0.50 | 2.0 | −5 |
| L | 1.0 | | 23 |
| L + A | 1.0 | 0.25 | 8 |
| L + A | 1.0 | 0.50 | 8 |
| L + A | 1.0 | 1.0 | 4 |
| L + A | 1.0 | 2.0 | 7 |
| O | 0.02 | | 37 |
| O + A | 0.02 | 0.25 | 30 |
| O + A | 0.02 | 0.50 | 7 |
| O + A | 0.02 | 1.0 | 16 |
| O + A | 0.02 | 2.0 | 9 |
| O | 0.04 | | 52 |
| O + A | 0.04 | 0.25 | 54 |
| O + A | 0.04 | 0.50 | 50 |
| O + A | 0.04 | 1.0 | 45 |
| O + A | 0.04 | 2.0 | 56 |
| Q | 0.10 | | 12 |
| Q + A | 0.10 | 0.25 | −5 |
| Q + A | 0.10 | 0.50 | 1 |
| Q + A | 0.10 | 1.0 | −3 |
| Q + A | 0.10 | 2.0 | 5 |
| Q | 0.20 | | 34 |
| Q + A | 0.20 | 0.25 | 32 |
| Q + A | 0.20 | 0.50 | 36 |
| Q + A | 0.20 | 1.0 | 29 |

TABLE XIII-continued

| Treatment | Rate (kg/ha) | (mg/g of seed) | % Growth Reduction |
|---|---|---|---|
| Q + A | 0.20 | 2.0 | 32 |
| R | 0.20 | | 18 |
| R + A | 0.20 | 0.25 | 16 |
| R + A | 0.20 | 0.50 | 13 |
| R + A | 0.20 | 1.0 | 12 |
| R + A | 0.20 | 2.0 | 12 |
| S | 0.50 | | 14 |
| S + A | 0.50 | 0.25 | 11 |
| S + A | 0.50 | 0.50 | 1 |
| S + A | 0.50 | 1.0 | 6 |
| S + A | 0.50 | 2.0 | 7 |
| S | 1.0 | | 21 |
| S + A | 1.0 | 0.25 | 19 |
| S + A | 1.0 | 0.50 | 19 |
| S + A | 1.0 | 1.0 | 21 |
| S + A | 1.0 | 2.0 | 20 |

EXAMPLE 14

Evaluation of α-Carboxy-5-[(2-chloro-α,α,α-trifluoro-p-tolyl)oxy]-o-anisic acid, dimethyl ester as a seed treatment for injury to rice caused by postemergence application of herbicides Rice seeds (Tebonnet) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of rice seed and shaken thoroughly to provide seed treatment rates equivalent to 0.25 to 4.0 mg of safener per gram of seed. Seeds are dried, planted in soil, placed on greenhouse benches, watered and cared for in accordance with conventional greenhouse procedures. At the 1 to 2 leaf stage, the rice plants are sprayed with a herbicide formulation. The herbicide spray formulation is diluted with water to provide the equivalent of 0.008 kg/ha to 0.50 kg/ha of herbicide to the foliage when applied through a spray nozzle operating at 40 psi for a predetermined time. The herbicide spray formulation contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered after 48 hours and cared for in accordance with conventional greenhouse procedures. After 14 days, the tests are terminated and each pot is examined and rated by measuring the height of the foliage. The test results are averaged and expressed as a percent growth reduction compared to an untreated check, as described in Example 1.

The results are summarized in Table XIV wherein

A is α-carboxy-5-[(2-chloro-α,α,α-trifluoro-p-tolyl)oxy]-o-anisic acid, dimethyl ester;

D is 2-(4-isopropyl-4-methyl-5-oxo-2-imidazolin-2-yl)-3-quinolinecarboxylic acid;

H is methyl o-{{3-[4,6-bis(difluoromethoxy)-2-pyrimidinyl]ureido}sulfonyl}benzoate;

O is methyl 2-{p-{[3-chloro-5-(trifluoromethyl)-2-pyridyl]oxy}phenoxy}propionate;

Q is the 2-(O-ethyloxime) of 2-butyryl-5-[2-(ethylthio)-propyl]-3-hydroxy-2-cyclohexen-1-one; and S is 3-(3,4-dichlorophenyl)-1,1-dimethylurea.

TABLE XIV

| Treatment | Rate (kg/ha) | (mg/g of seed) | % Growth Reduction |
|---|---|---|---|
| D | 0.01 | | 24 |
| D + A | 0.01 | 0.25 | −13 |
| D + A | 0.01 | 0.50 | −18 |
| D + A | 0.01 | 1.0 | −5 |
| D + A | 0.01 | 2.0 | 6 |
| D + A | 0.01 | 4.0 | 18 |
| D | 0.025 | | 49 |
| D + A | 0.025 | 0.25 | 35 |
| D + A | 0.025 | 0.50 | 40 |
| D + A | 0.025 | 1.0 | 53 |
| D + A | 0.025 | 2.0 | 52 |
| D + A | 0.025 | 4.0 | 40 |
| H | 0.016 | | 40 |
| H + A | 0.016 | 0.25 | 38 |
| H + A | 0.016 | 0.50 | 34 |
| H + A | 0.016 | 1.0 | 38 |
| H + A | 0.016 | 2.0 | 36 |
| H | 0.032 | | 44 |
| H + A | 0.032 | 0.25 | 44 |
| H + A | 0.032 | 0.50 | 45 |
| H + A | 0.032 | 1.0 | 50 |
| H + A | 0.032 | 2.0 | 54 |
| O | 0.008 | | 24 |
| O + A | 0.008 | 0.25 | 23 |
| O + A | 0.008 | 0.50 | 20 |
| O + A | 0.008 | 1.0 | 8 |
| O + A | 0.008 | 2.0 | 15 |
| O | 0.016 | | 30 |
| O + A | 0.016 | 0.25 | 22 |
| O + A | 0.016 | 0.50 | 28 |
| O + A | 0.016 | 1.0 | 32 |
| O + A | 0.016 | 2.0 | 24 |
| Q | 0.075 | | 30 |
| Q + A | 0.075 | 0.25 | 34 |
| Q + A | 0.075 | 0.50 | 33 |
| Q + A | 0.075 | 1.0 | 20 |
| Q + A | 0.075 | 2.0 | 13 |
| Q | 0.15 | | 44 |
| Q + A | 0.15 | 0.25 | 35 |
| Q + A | 0.15 | 0.50 | 34 |
| Q + A | 0.15 | 1.0 | 42 |
| Q + A | 0.15 | 2.0 | 41 |
| S | 0.25 | | 38 |
| S + A | 0.25 | 0.25 | 34 |
| S + A | 0.25 | 0.50 | 32 |
| S + A | 0.25 | 1.0 | 34 |
| S + A | 0.25 | 2.0 | 25 |
| S | 0.50 | | 60 |
| S + A | 0.50 | 0.25 | 63 |
| S + A | 0.50 | 0.50 | 68 |
| S + A | 0.50 | 1.0 | 70 |
| S + A | 0.50 | 2.0 | 70 |

EXAMPLE 15

Evaluation of α-Carboxy-5-[(2-chloro-α,α,α-trifluoro-p-tolyl)oxy]-o-anisic acid, dimethyl ester as a seed treatment for injury to corn caused by preemergence application of herbicides Corn seeds (Pioneer 3475) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 62.5 μL to 1.0 mL are made up to 1 mL with an acetone:dimethylformamide (10:1) mixture, added to 10 g of corn seed and shaken thoroughly to provide seed treatment rates equivalent to 0.25 to 4.0 mg of safener per gram of seed. Seeds are dried and planted in soil. The soil surface is moistened and sprayed preemergence with a herbicide solution. The herbicide spray solution is diluted with water to provide the equivalent of 2.0 kg/ha to 5.0 kg/ha of herbicide to the soil surface when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in Example 1.

The results are summarized in Table XV wherein

A is α-carboxy-5-[(2-chloro-α,α,α-trifluoro-p-tolyl)oxy]-o-anisic acid, dimethyl ester;

T is N-(1-ethylpropyl)-2,6-dinitro-3,4-xylidine; and

U is 2-chloro-6'-ethyl-N-(2-methoxy-1-methylethyl)-o-acetotoluidide.

TABLE XV

| Treatment | Rate (kg/ha) | (mg/g of seed) | % Growth Reduction |
|---|---|---|---|
| T | 2.5 | | 20 |
| T + A | 2.5 | 0.25 | 9 |
| T + A | 2.5 | 0.50 | 10 |
| T + A | 2.5 | 1.0 | 8 |
| T + A | 2.5 | 2.0 | 11 |
| T | 5.0 | | 43 |
| T + A | 5.0 | 0.25 | 23 |
| T + A | 5.0 | 0.50 | 30 |
| T + A | 5.0 | 1.0 | 42 |
| T + A | 5.0 | 2.0 | 42 |
| U | 2.0 | | 38 |
| U + A | 2.0 | 0.25 | 13 |
| U + A | 2.0 | 0.50 | 10 |
| U + A | 2.0 | 1.0 | 14 |
| U + A | 2.0 | 2.0 | 15 |
| U | 4.0 | | 53 |
| U + A | 4.0 | 0.25 | 26 |
| U + A | 4.0 | 0.50 | 26 |
| U + A | 4.0 | 1.0 | 16 |
| U + A | 4.0 | 2.0 | 19 |

EXAMPLE 16

Evaluation of α-Carboxy-5-[(2-chloro-α,α,α-trifluoro-p-tolyl)oxy]-o-anisic acid, dimethyl ester as a seed treatment for injury to oats caused by preemergence application of herbicides Tame oat seeds (Porter) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 25.0 μL to 0.5 mL are made up to 1 mL with an acetone:dimethylformamide (10:1) mixture, added to 10 g of seed and shaken thoroughly to provide seed treatment rates equivalent to 0.10 to 2.0 mg of safener per gram of seed. Seeds are dried and planted in soil. The soil surface is moistened and sprayed preemergence with a herbicide solution. The herbicide spray solution is diluted with water to provide the equivalent of 0.50 kg/ha to 5.0 kg/ha of herbicide to the soil surface when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in Example 1.

The results are summarized in Table XVI wherein

A is α-carboxy-5-[(2-chloro-α,α,α-trifluoro-p-tolyl)oxy]-o-anisic acid, dimethyl ester;

T is N-(1-ethylpropyl)-2,6-dinitro-3,4-xylidine;

U is 2-chloro-6'-ethyl-N-(2-methoxy-1-methylethyl)-o-acetotoluidide; and

V is ethyl dipropylthiolcarbamate.

TABLE XVI

| Treatment | Rate (kg/ha) | (mg/g of seed) | % Growth Reduction |
|---|---|---|---|
| T | 3.0 | | 23 |
| T + A | 3.0 | 0.10 | 33 |
| T + A | 3.0 | 0.25 | 31 |
| T + A | 3.0 | 0.50 | 21 |
| T + A | 3.0 | 1.0 | 41 |
| T + A | 3.0 | 2.0 | 37 |
| T | 5.0 | | 36 |
| T + A | 5.0 | 0.10 | 25 |
| T + A | 5.0 | 0.25 | 31 |
| T + A | 5.0 | 0.50 | 50 |
| T + A | 5.0 | 1.0 | 48 |
| T + A | 5.0 | 2.0 | 54 |
| U | 1.0 | | 34 |
| U + A | 1.0 | 0.10 | 40 |
| U + A | 1.0 | 0.25 | 38 |
| U + A | 1.0 | 0.50 | 52 |
| U + A | 1.0 | 1.0 | 53 |
| U + A | 1.0 | 2.0 | 57 |
| U | 2.0 | | 69 |
| U + A | 2.0 | 0.10 | 76 |
| U + A | 2.0 | 0.25 | 79 |
| U + A | 2.0 | 0.50 | 84 |
| U + A | 2.0 | 1.0 | 61 |
| U + A | 2.0 | 2.0 | 46 |
| V | 0.50 | | 18 |
| V + A | 0.50 | 0.10 | 15 |
| V + A | 0.50 | 0.25 | 10 |
| V + A | 0.50 | 0.50 | 1 |
| V + A | 0.50 | 1.0 | −3 |
| V + A | 0.50 | 2.0 | 33 |
| V | 1.0 | | 61 |
| V + A | 1.0 | 0.10 | 88 |
| V + A | 1.0 | 0.25 | 92 |
| V + A | 1.0 | 0.50 | 90 |
| V + A | 1.0 | 1.0 | 85 |
| V + A | 1.0 | 2.0 | 88 |

EXAMPLE 17

Evaluation of α-Carboxy-5-[(2-chloro-α,α,α-trifluoro-p-tolyl)oxy]-o-anisic acid, dimethyl ester as a seed treatment for injury to wheat caused by preemergence application of 2-chloro-6'-ethyl-N-(2-methoxy-1-methylethyl)-o-acetotoluidide Wheat seeds (Wakooma) are treated with the safener α-carboxy-5-[(2-chloro-α,α,α-trifluoro-p-tolyl)oxy]-o-anisic acid, dimethyl ester by first making a stock solution of 100 mg of the safener in 2.5 mL of an acetone:dimethylformamide (5:1) mixture. Aliquots of the stock solution ranging from 25.0 μL to 0.5 mL are made up to 1 mL with an acetone:dimethylformamide (10:1) mixture, added to 10 g of wheat seed and shaken thoroughly to provide seed treatment rates equivalent to 0.10 to 2.0 mg of safener per gram of seed. Seeds are dried and planted in soil. The soil surface is moistened and sprayed preemergence with a 2-chloro-6'-ethyl-N-(2-methoxy-1-methylethyl) -o-acetotoluidide solution. The 2-chloro-6'-ethyl-N -(2-methoxy-1-methylethyl)-o-aceto-toluidide spray solution is diluted with water to provide the equivalent of 0.30 kg/ha to 0.60 kg/ha of 2-chloro-6'-ethyl-N-(2-methoxy-1-methylethyl)-o-aceto-toluidide to the soil surface when applied through a spray nozzle operating at 40 psi for a predetermined time. The 2-chloro-6'-ethyl-N-(2-methoxy-11-methylethyl)-o-aceto-toluidide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures.

Twenty-one days after treatment, the tests are terminated and each pot is examined and rated by measuring the height of the foliage. The test results are averaged and expressed as a percent growth reduction compared to an untreated check, as described in Example 1.

The results are summarized in Table XVII wherein

A is α-carboxy-5-[(2-chloro-α,α,α-trifluoro-p-tolyl)oxy]-o-anisic acid, dimethyl ester; and U is 2-chloro-6'-ethyl-N-(2-methoxy-1-methylethyl)-o-acetotoluidide.

TABLE XVII

| Treatment | Rate (kg/ha) | (mg/g of seed) | % Growth Reduction |
|---|---|---|---|
| U | 0.30 | | 64 |
| U + A | 0.30 | 0.10 | 72 |
| U + A | 0.30 | 0.25 | 65 |
| U + A | 0.30 | 0.50 | 65 |
| U + A | 0.30 | 1.0 | 51 |
| U + A | 0.30 | 2.0 | 41 |
| U | 0.60 | | 75 |
| U + A | 0.60 | 0.10 | 74 |
| U + A | 0.60 | 0.25 | 81 |
| U + A | 0.60 | 0.50 | 71 |
| U + A | 0.60 | 1.0 | 81 |
| U + A | 0.60 | 2.0 | 66 |

EXAMPLE 18

Evaluation of α-Carboxy-5-[(2-chloro-α,α,α-trifluoro-p-tolyl)oxy]-o-anisic acid, dimethyl ester as a seed treatment for injury to corn caused by preplant incorporation of herbicides Three inch square pots are filled with 150 mL of Sassafras soil containing 17% sand and sprayed with a herbicide solution. The herbicide spray solution is diluted with water to provide the equivalent of 1.0 kg/ha to 4.0 kg/ha of herbicide to the soil surface when applied through a spray nozzle operating at 40 psi for a predetermined time. After the soil is sprayed, it is poured into a plastic basin and mixed. The pots are refilled with 100 mL of the treated soil. Corn seeds (Pioneer 3475) are treated with the safener α-carboxy-5-[(2-chloro-α,α,α-trifluoro-p-tolyl)oxy]-o -anisic acid, dimethyl ester according to the procedure described in Example 9, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in Example 1.

The results are summarized in Table XVIII wherein

A is α-carboxy-5-[(2-chloro-α,α,α-trifluoro-p-tolyl)oxy]-o-anisic acid, dimethyl ester;

T is N-(1-ethylpropyl)-2,6-dinitro-3,4-xylidine;

U is 2-chloro-6'-ethyl-N-(2-methoxy-1-methylethyl)-o-acetotoluidide; and

V is ethyl dipropylthiolcarbamate.

TABLE XVIII

| Treatment | Rate (kg/ha) | (mg/g of seed) | % Growth Reduction |
|---|---|---|---|
| T | 1.0 | | 29 |
| T + A | 1.0 | 0.10 | 11 |
| T + A | 1.0 | 0.25 | 17 |
| T + A | 1.0 | 0.50 | 25 |
| T + A | 1.0 | 1.0 | 22 |
| T + A | 1.0 | 2.0 | 28 |
| T | 2.0 | | 42 |
| T + A | 2.0 | 0.10 | 48 |
| T + A | 2.0 | 0.25 | 37 |
| T + A | 2.0 | 0.50 | 38 |
| T + A | 2.0 | 1.0 | 39 |
| T + A | 2.0 | 2.0 | 41 |
| U | 2.0 | | 21 |
| U + A | 2.0 | 0.10 | 11 |
| U + A | 2.0 | 0.25 | 12 |
| U + A | 2.0 | 0.50 | 0 |
| U + A | 2.0 | 1.0 | −1 |
| U + A | 2.0 | 2.0 | 1 |
| U | 4.0 | | 38 |
| U + A | 4.0 | 0.10 | 13 |
| U + A | 4.0 | 0.25 | −2 |
| U + A | 4.0 | 0.50 | 6 |
| U + A | 4.0 | 1.0 | 13 |
| U + A | 4.0 | 2.0 | −2 |
| V | 2.0 | | 14 |
| V + A | 2.0 | 0.10 | 0 |
| V + A | 2.0 | 0.25 | 0 |
| V + A | 2.0 | 0.50 | 4 |
| V + A | 2.0 | 1.0 | −4 |
| V + A | 2.0 | 2.0 | −5 |
| V | 4.0 | | 44 |
| V + A | 4.0 | 0.10 | 41 |
| V + A | 4.0 | 0.25 | 19 |
| V + A | 4.0 | 0.50 | 20 |
| V + A | 4.0 | 1.0 | 12 |
| V + A | 4.0 | 2.0 | 8 |

EXAMPLE 19

Evaluation of α-Carboxy-5-[(2-chloro-α,α,α-trifluoro-p-tolyl)oxy]-o-anisic acid, dimethyl ester as a seed treatment for injury to barley caused by preplant incorporation of herbicides Three inch square pots are filled with 150 mL of Sassafras soil containing 17% sand and sprayed with a herbicide solution. The herbicide spray solution is diluted with water to provide the equivalent of 0.5 kg/ha to 4.0 kg/ha of herbicide to the soil surface when applied through a spray nozzle operating at 40 psi for a prede-termined time. After the soil is sprayed, it is poured into a plastic basin and mixed. The pots are refilled with 100 mL of the treated soil. Barley seeds (Volga) are treated with the safener α-carboxy-5-[(2-chloro-α,α,α-trifluoro-p-tolyl)oxy]-o-anisic acid, dimethyl ester according to the procedure described in Example 10, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in Example 1.

The results are summarized in Table XIX wherein

A is α-carboxy-5-[(2-chloro-α,α,α-trifluoro-p-tolyl)oxy]-o-anisic acid, dimethyl ester;

U is 2-chloro-6'-ethyl-N-(2-methoxy-1-methylethyl)-o-acetotoluidide; and

V is ethyl dipropylthiolcarbamate.

TABLE XIX

| Treatment | Rate (kg/ha) | (mg/g of seed) | % Growth Reduction |
|---|---|---|---|
| U | 2.0 | | 54 |
| U + A | 2.0 | 0.10 | 61 |
| U + A | 2.0 | 0.25 | 30 |
| U + A | 2.0 | 0.50 | 34 |
| U + A | 2.0 | 1.0 | 21 |
| U + A | 2.0 | 2.0 | 43 |
| U | 4.0 | | 72 |
| U + A | 4.0 | 0.10 | 72 |
| U + A | 4.0 | 0.25 | 67 |
| U + A | 4.0 | 0.50 | 31 |
| U + A | 4.0 | 1.0 | 26 |
| U + A | 4.0 | 2.0 | 35 |
| V | 0.50 | | 50 |
| V + A | 0.50 | 0.10 | −9 |
| V + A | 0.50 | 0.25 | 0 |
| V + A | 0.50 | 0.50 | −10 |
| V + A | 0.50 | 1.0 | −12 |
| V + A | 0.50 | 2.0 | 1 |
| V | 1.0 | | 86 |
| V + A | 1.0 | 0.10 | 48 |
| V + A | 1.0 | 0.25 | 78 |
| V + A | 1.0 | 0.50 | 55 |
| V + A | 1.0 | 1.0 | 55 |
| V + A | 1.0 | 2.0 | 37 |

EXAMPLE 20

Evaluation of α-Carboxy-5-[(2-chloro-α,α,α-trifluoro-p-tolyl)oxy]-o-anisic acid, dimethyl ester as a seed treatment for injury to oats caused by preplant incorporation of herbicides Three inch square pots are filled with 150 mL of Sassafras soil containing 17% sand and sprayed with a herbicide solution. The herbicide spray solution is diluted with water to provide the equivalent of 0.125 kg/ha to 3.0 kg/ha of herbicide to the soil surface when applied through a spray nozzle operating at 40 psi for a prede-termined time. After the soil is sprayed, it is poured into a plastic basin and mixed. The pots are refilled with 100 mL of the treated soil. Oat seeds (Porter) are treated with the safener α-carboxy-5-[(2-chloro-α,α,α-trifluoro-p-tolyl)oxy]-o-anisic acid, dimethyl ester according to the procedure described in Example 11, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in Example 1.

The results are summarized in Table XX wherein

A is α-carboxy-5-[(2-chloro-α,α,α-trifluoro-p-tolyl)oxy]-o-anisic acid, dimethyl ester;

T is N-(1-ethylpropyl)-2,6-dinitro-3,4-xylidine;

U is 2-chloro-6'-ethyl-N-(2-methoxy-1-methylethyl)-o-acetotoluidide; and

V is ethyl dipropylthiolcarbamate.

TABLE XX

| Treatment | Rate (kg/ha) | (mg/g of seed) | % Growth Reduction |
|---|---|---|---|
| T | 0.25 | | 15 |
| T + A | 0.25 | 0.10 | 11 |
| T + A | 0.25 | 0.25 | 20 |
| T + A | 0.25 | 0.50 | 19 |
| T + A | 0.25 | 1.0 | 18 |
| T + A | 0.25 | 2.0 | 16 |
| T | 0.50 | | 88 |
| T + A | 0.50 | 0.10 | 83 |
| T + A | 0.50 | 0.25 | 84 |
| T + A | 0.50 | 0.50 | 79 |
| T + A | 0.50 | 1.0 | 68 |
| T + A | 0.50 | 2.0 | 44 |
| U | 1.5 | | 70 |
| U + A | 1.5 | 0.10 | 68 |
| U + A | 1.5 | 0.25 | 74 |
| U + A | 1.5 | 0.50 | 51 |
| U + A | 1.5 | 1.0 | 48 |
| U + A | 1.5 | 2.0 | 32 |
| U | 3.0 | | 86 |
| U + A | 3.0 | 0.10 | 89 |
| U + A | 3.0 | 0.25 | 84 |
| U + A | 3.0 | 0.50 | 87 |
| U + A | 3.0 | 1.0 | 81 |
| U + A | 3.0 | 2.0 | 74 |
| V | 0.125 | | 44 |
| V + A | 0.125 | 0.10 | 31 |
| V + A | 0.125 | 0.25 | 34 |
| V + A | 0.125 | 0.50 | 30 |
| V + A | 0.125 | 1.0 | 35 |
| V + A | 0.125 | 2.0 | 21 |
| V | 0.25 | | 88 |
| V + A | 0.25 | 0.10 | 83 |
| V + A | 0.25 | 0.25 | 82 |
| V + A | 0.25 | 0.50 | 78 |
| V + A | 0.25 | 1.0 | 77 |
| V + A | 0.25 | 2.0 | 67 |

EXAMPLE 21

Evaluation of α-Carboxy-5-[(2-chloro-α,α,
α-trifluoro-p-tolyl)oxy]-o-anisic acid, dimethyl ester
as a preplant incorporation treatment for injury to
corn caused by preplant incorporation of herbicides Three inch square pots are filled with 150 mL of Sassafras soil containing 17% sand and sprayed with a formulation of the appropriate herbicide, or a formulation of the appropriate herbicide mixed with a formulation of α-carboxy-5-[(2-chloro-α,α,α-trifluoro-p-tolyl)oxy]-o-anisic acid, dimethyl ester. The herbicide and safener are diluted with water to provide the equivalent of 1.0 kg/ha to 4.5 kg/ha of herbicide and 0.032 kg/ha to 0.50 kg/ha of safener to the soil surface when applied through a spray nozzle operating at 40 psi for a predetermined time. After the soil is sprayed, it is poured into a plastic basin and mixed. The pots are refilled with 100 mL of the treated soil. Corn seeds (Pioneer 3475) are planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in Example 1.

The results are summarized in Table XXI wherein

A is α-carboxy-5-[(2-chloro-α,α,α-trifluoro-p-tolyl)oxy]-o-anisic acid, dimethyl ester;

T is N-(1-ethylpropyl)-2,6-dinitro-3,4-xylidine; and

U is 2-chloro-6'-ethyl-N-(2-methoxy-1-methylethyl)-o-acetotoluidide.

TABLE XXI

| Treatment | Rate (kg/ha) | % Growth Reduction |
|---|---|---|
| T | 1.0 | 45 |
| T + A | 1.0 + 0.032 | 34 |
| T + A | 1.0 + 0.063 | 32 |
| T + A | 1.0 + 0.125 | 31 |
| T + A | 1.0 + 0.25 | 47 |
| T + A | 1.0 + 0.50 | 30 |
| U | 4.5 | 63 |
| U + A | 4.5 + 0.032 | 54 |
| U + A | 4.5 + 0.063 | 67 |
| U + A | 4.5 + 0.125 | 60 |
| U + A | 4.5 + 0.25 | 40 |
| U + A | 4.5 + 0.50 | 51 |

EXAMPLE 22

Evaluation of α-Carboxy-5-[(2-chloro-α,α,
α-trifluoro-p-tolyl)oxy]-o-anisic acid, dimethyl ester
as a seed treatment for injury to sorghum caused
by preplant incorporation of
N-(1-ethylpropyl)-2,6-dinitro-3,4-xylidine Three inch square pots are filled with 150 mL of Sassafras soil containing 17% sand and sprayed with a N-(1-ethylpropyl)-2,6-dinitro-3,4-xylidine solution. The N-(1-ethylpropyl)-2,6-dinitro-3,4-xylidine spray solution is diluted with water to provide the equivalent of 2.0 kg/ha to 4.0 kg/ha of N-(1-ethylpropyl)-2,6-dinitro-3,4-xylidine to the soil surface when applied through a spray nozzle operating at 40 psi for a predetermined time. After the soil is sprayed, it is poured into a plastic basin and mixed. The pots are refilled with 100 mL of the treated soil. Sorghum seeds (NC 271) are treated with the safener α-carboxy-5-[(2-chloro-α,α, α-trifluoro-p-tolyl)oxy]-o-anisic acid, dimethyl ester according to the procedure described in Example 12, planted in the treated soil and covered with the remaining 50 mL of treated soil. Pots are then placed on greenhouse benches, watered and cared for in accordance with conventional greenhouse procedures.

Twenty-one days after planting, the tests are terminated and each pot is examined and rated by measuring the height of the foliage. The test results are averaged and expressed as a percent growth reduction compared to an untreated check, as described in Example 1.

The results are summarized in Table XXII wherein

A is α-carboxy-5-[(2-chloro-α,α,α-trifluoro-p-tolyl)oxy]-o-anisic acid, dimethyl ester; and T is N-(1-ethylpropyl)-2,6-dinitro-3,4-xylidine.

TABLE XXII

| Treatment | Rate (kg/ha) | Rate (mg/g of seed) | % Growth Reduction |
|---|---|---|---|
| T | 2.0 | | 17 |
| T + A | 2.0 | 0.10 | 17 |
| T + A | 2.0 | 0.25 | 9 |
| T + A | 2.0 | 0.50 | 12 |
| T + A | 2.0 | 1.0 | 19 |
| T + A | 2.0 | 2.0 | 8 |
| T | 4.0 | | 37 |
| T + A | 4.0 | 0.10 | 25 |
| T + A | 4.0 | 0.25 | 25 |
| T + A | 4.0 | 0.50 | 27 |
| T + A | 4.0 | 1.0 | 28 |
| T + A | 4.0 | 2.0 | 13 |

EXAMPLE 23

Evaluation of test compounds as safeners for corn
injury from postemergence applications of
5-ethyl-2-(4-isopropyl-4-methyl-5-oxo-
2-imidazolin-2-yl)nicotinic acid Corn plants (Pioneer 3475) in the third leaf stage are sprayed with a solution of 5-ethyl-2-(4-isopropyl-4-methyl-5-oxo-2-imidazolin-2-yl)nicotinic acid or a solution of 5-ethyl-2-(4-isopropyl-4-methyl -5-oxo-2-imidazolin-2-yl)nicotinic acid mixed with a solution of a test compound. The 5-ethyl-2-(4-isopropyl-4-methyl-5-oxo-2-imidazolin-2-yl)nicotinic acid and test compound solutions are diluted with water to provide the equivalent of 0.05 kg/ha of 5-ethyl-2-(4-isopropyl-4-methyl-5-oxo-2-imidazolin-2-yl)nicotinic acid and 0.032 kg/ha to 0.50 kg/ha of test compound to the foliage when applied through a spray nozzle operating at 40 psi for a predetermined time. The herbicide spray solution contains 0.25% of the spray adjuvant ORTHO X-77, a non-ionic wetting agent containing alkylaryl polyoxyethylene, glycols, free fatty acids and isopropanol, manufactured by Valent USA Corp. Pots are then placed on greenhouse benches, watered and cared for in accordance with conventional greenhouse procedures. From 3 to 4 weeks after treatment, the tests are terminated and each pot is examined and rated by measuring the height of the foliage. The test results are averaged and expressed as a ratio of the height of the safener and herbicide treated plants divided by the height of the herbicide alone treated plants. A ratio greater than one indicates that the test compound is a safener.

The results are summarized in Table XXIII wherein

A is 2-(1-carboxyethoxy)-5-[(2-chloro -α,α,α-trifluoro-p-tolyl)oxy]benzoic acid;

B is 2-(1-carboxyethoxy)-5-[(2-chloro -α,α,α-trifluoro-p-tolyl)oxy]benzoic acid, dimethyl ester;

C is 2-(carboxymethoxy)-5-[(α,α,α-trifluoro-p-tolyl)oxy]benzoic acid, dimethyl ester;

D is 2-(carboxymethoxy)-5-[(5,6-dichloro-α, α,α-trifluoro-m-tolyl)oxy]benzoic acid, dimethyl ester;

E is 2-(carboxymethoxy)-5-[(5,6-dichloro-α, α,α-trifluoro-m-tolyl)oxy]benzoic acid;

F is 2-(carboxymethoxy)-5-[(α,α,α-trifluoro -p-tolyl)oxy]benzoic acid;

G is methyl 5-[(2-chloro-α,α,α-trifluoro-p -tolyl)oxy]-2-(2-oxopropoxy)benzoate;

H is α-carboxy-5-[(2-chloro-α,α,α-trifluoro-p-tolyl)oxy] -o-anisic acid, dimethyl ester;

I is 2-(carboxymethoxy)-5-[(2-chloro-α,α, α-trifluoro-p-tolyl)oxy]benzoic acid, diethyl ester;

J is 2-(carboxymethoxy)-5-[(2-chloro-α,α, α-trifluoro-p-tolyl)oxy]benzoic acid, diisopropyl ester;

K is 2-(carboxymethoxy)-5-[(2-chloro-α,α, α-trifluoro-p-tolyl)oxy]benzoic acid, diallyl ester;

L is 2-(4-carboxybutoxy)-5-[(2-chloro -α,α,α-trifluoro-p-tolyl)oxy]benzoic acid, dimethyl ester;

M is 2-(carboxymethoxy)-5-[(2-chloro-α,α, α-trifluoro-p-tolyl)oxy]benzoic acid;

N is 2-(carboxymethoxy)-5-[(2-chloro-α,α, α-trifluoro-p-tolyl)oxy]benzoic acid, diammonium salt;

O is 2-(carboxymethoxy)-5-[(2-chloro-α,α, α-trifluoro-p-tolyl)oxy]benzoic acid, 2-tert-butyl methyl ester;

P is {2-acetyl-4-[(2-chloro-α,α,α, 6-tetrafluoro-p-tolyl)oxy]phenoxy}acetic acid;

Q is 2-(carboxymethoxy)-5-[(2-chloro-α,α, α,6-tetrafluoro-p-tolyl)oxy]benzoic acid;

R is 2-(carboxymethoxy)-5-[(2-chloro-α,α, α-trifluoro-p-tolyl)oxy]benzoic acid, diisopropylammonium salt;

S is 2-(carboxymethoxy)-5-[(2-chloro-α,α, α-trifluoro-p-tolyl)oxy]benzoic acid, disodium salt;

T is 2-(carboxymethoxy)-5-[(2-chloro-α,α, α-trifluoro-p-tolyl)oxy]benzoic acid, 1-methyl ester;

U is methyl {2-acetyl-4-[(2-chloro-α,α, α,6-tetrafluoro-p-tolyl)oxy]phenoxy}acetate;

V is 2-carboxy-4-[(2-chloro-α,α,α-trifluoro-p-tolyl)oxy] cinnamic acid, dimethyl ester;

W is 2-(carboxymethoxy)-5-[(α,α,α,2-tetrafluoro-p-tolyl)oxy]benzoic acid;

X is 2-(4-carboxybutoxy)-5-[(2-chloro -α,α,α-trifluoro-p-tolyl)oxy]benzoic acid;

Y is α-carboxy-5-{[3-chloro-5-(trifluoromethyl)-2-pyridyl]oxy}-o-anisic acid;

Z is 2-carboxy-4-[(2-chloro-α,α,α-trifluoro-p-tolyl)oxy] cinnamic acid; and

AA is 2-(1-carboxybutoxy)-5-[(2-chloro -α,α,α-trifluoro-p-tolyl)oxy]benzoic acid.

TABLE XXIII

| Test Compound | RATIO (treated/untreated) Rate of Test Compound (kg/ha) | | | | |
|---|---|---|---|---|---|
| | 0.032 | 0.063 | 0.125 | 0.250 | 0.500 |
| A | — | 2.06 | 2.40 | 2.84 | 2.77 |
| B | — | 1.29 | 1.36 | 1.52 | 2.42 |
| C | 1.52 | 1.29 | 1.57 | 1.67 | 2.10 |
| D | 1.52 | 2.52 | 2.00 | 2.29 | 2.67 |
| E | 1.52 | 1.43 | 1.91 | 2.00 | 2.67 |
| F | 1.71 | 1.33 | 1.38 | 1.57 | 2.29 |
| G | 1.91 | 1.30 | 1.57 | 2.44 | 2.78 |
| H | 1.26 | 1.44 | 1.50 | 1.56 | 1.69 |
| I | 1.39 | 1.57 | 1.64 | 1.63 | 1.79 |
| J | 1.02 | 1.43 | 1.45 | 1.21 | 1.55 |
| K | 1.43 | 1.61 | 1.41 | 1.70 | 1.63 |
| L | 1.17 | 1.00 | 1.14 | 1.11 | 1.39 |
| M | — | 0.89 | 0.94 | 1.17 | 1.60 |
| N | 0.74 | 0.67 | 0.88 | 1.43 | 1.88 |
| O | 1.12 | 0.98 | 0.98 | 1.36 | 1.30 |
| P | 0.83 | 0.67 | 1.14 | 1.11 | 1.50 |
| Q | — | 0.71 | 0.91 | 0.97 | 1.11 |
| R | 0.71 | 0.67 | 0.67 | 0.83 | 1.62 |
| S | 0.69 | 0.71 | 0.79 | 1.12 | 1.05 |
| T | 0.44 | 0.30 | 0.89 | 1.09 | 1.34 |
| U | 0.86 | 0.69 | 0.89 | 0.86 | 1.50 |
| V | 1.36 | 0.97 | 0.78 | 1.15 | 1.56 |
| W | 1.83 | 1.60 | 1.28 | 1.24 | 1.20 |
| X | 0.89 | 1.37 | 1.61 | 1.39 | 1.42 |
| Y | 0.47 | 0.47 | 0.56 | 0.97 | 1.15 |
| Z | 1.37 | 1.24 | 1.24 | 0.60 | 0.74 |
| AA | 0.83 | 0.82 | 0.97 | 1.02 | 1.17 |

— = no evaluation

EXAMPLE 24

Evaluation of test compounds applied as seed treatments for injury to wheat caused by preplant incorporation of N-(1-ethylpropyl)-2,6-dinitro-3,4-xylidine Three inch square pots are filled with 150 mL of Sassafras soil containing 17% sand and sprayed with a N-(1-ethylpropyl)-2,6-dinitro-3,4-xylidine solution. The N-(1-ethylpropyl)-2,6-dinitro-3,4-xylidine spray solution is diluted with water to provide the equivalent of 0.25 kg/ha of active ingredient to the soil surface when applied through a spray nozzle operating at 40 psi for a predetermined time. After the soil is sprayed, it is poured into a plastic basin and mixed. Fifteen mL test tubes are filled with about ten mL of the treated soil. Wheat seeds (Sceptre) are treated with test compounds according to the procedure described in Example 13 and planted in the treated soil in the test tubes. The test tubes are then placed in a growth chamber.

Seven to ten days after planting, the tests are terminated and each test tube is examined by measuring the length of the wheat root. The test results are averaged and expressed as a ratio of the root length of the safener and herbicide treated plants divided by the root length of the herbicide alone treated plants. A ratio greater than one indicates that the test compound is a safener.

The results are summarized in Table XXIV wherein

A is α-carboxy-5-[(2-chloro-α,α,α-trifluoro-p-tolyl)oxy] -o-anisic acid, dimethyl ester;

B is 2-(carboxymethoxy)-5-[(2-chloro-α, α,α-trifluoro-p-tolyl)oxy]benzoic acid;

C is 2-(1-carboxyethoxy)-5-[(2-chloro -α,α,α-trifluoro-p-tolyl)oxy]benzoic acid;

D is 2-(carboxymethoxy)-5-[(2-chloro-α, α,α,6-tetrafluoro-p-tolyl)oxy]benzoic acid;

E is 2-(carboxymethoxy)-5-[(α,α,α,2-tetrafluoro-p-tolyl)oxy]benzoic acid, dimethyl ester;

F is 2-(carboxymethoxy)-5-[(α,α,α,2-tetrafluoro-p-tolyl)oxy]benzoic acid;

G is 2-(carboxymethoxy)-5-[(5,6-dichloro-α, α,α-trifluoro-m-tolyl)oxy]benzoic acid;

H is 2-(carboxymethoxy)-5-[(α,α,α-trifluoro-p-tolyl)oxy]benzoic acid;

I is 2-(carboxymethoxy)-5-[(2-chloro-α,α, α-trifluoro-p-tolyl)oxy]benzoic acid, diammonium salt;

J is 2-(carboxymethoxy)-5-[(2-chloro-α,α, α-trifluoro-p-tolyl)oxy]benzoic acid, diallyl ester;

K is 2-(carboxymethoxy)-5-[(2-chloro-α,α, α-trifluoro-p-tolyl)oxy]benzoic acid, 1-methyl ester;

L is 2-carboxy-4-[(2-chloro-α,α,α-trifluoro-p-tolyl)oxy] cinnamic acid;

M is 2-(1-carboxybutoxy)-5-[(2-chloro -α,α,α-trifluoro-p-tolyl)oxy]benzoic acid;

N is 2-[(1-carboxyhexyl)oxy]-5-[(2-chloro-α,α,α-trifluoro-p-tolyl)oxy]benzoic acid;

O is 2-(1-carboxy-3-phenylpropoxy)-5-[(2-chloro-α,α,α-trifluoro-p-tolyl)oxy]benzoic acid;

P is 2-[(α-carboxybenzyl)oxy]-5-[(2-chloro-α,α,α-trifluoro-p-tolyl)oxy]benzoic acid, dimethyl ester;

Q is 2-(1-carboxypropoxy)-5-[(2-chloro -α,α,α-trifluoro-p-tolyl)oxy]benzoic acid, dimethyl ester;

R is 2-(1-carboxypropoxy)-5-[(2-chloro -α,α,α-trifluoro-p-tolyl)oxy]benzoic acid, 2-ethyl methyl ester;

S is 2-[(1-carboxytridecyl)oxy]-5-[(2-chloro-α,α,α-trifluoro-p-tolyl)oxy]benzoic acid, 2-ethyl methyl ester;

T is 2-[(α-carboxybenzyl)oxy]-5-[(2-chloro-α,α,α-trifluoro-p-tolyl)oxy]benzoic acid;

U is 2-(1-carboxy-2-methylpropoxy)-5-[(2-chloro-α,α,α-trifluoro-p-tolyl)oxy]benzoic acid;

V is 2-[(1-carboxytridecyl)oxy]-5-[(2-chloro-α,α,α-trifluoro-p-tolyl)oxy]benzoic acid;

W is 5-[(2-chloro-α,α,α-trifluoro-p-tolyl) oxy]-2-[(tetrahydro-2-oxo-3-furyl)oxy]benzoic acid, methyl ester;

X is 2-(1-carboxypropoxy)-5-[(2-chloro -α,α,α-trifluoro-p-tolyl)oxy]benzoic acid;

Y is 2-(1-carboxy-3-phenylpropoxy)-5-[(2-chloro-α,α,α-trifluoro-p-tolyl)oxy]benzoic acid, 2-ethyl methyl ester;

Z is 5-[(2-chloro-α,α,α-trifluoro-p-tolyl) oxy]-2-[(tetrahydro-2-oxo-3-furyl)oxy]benzoic acid;

AA is 2-(1-carboxybutoxy)-5-[(2-chloro -α,α,α-trifluoro-p-tolyl)oxy]benzoic acid, diallyl ester; and BB is 2-(1-carboxybutoxy)-5-[(2-chloro -α,α,α-trifluoro-p-tolyl)oxy]benzoic acid, dibenzyl ester.

TABLE XXIV

| Test Compound | RATIO (treated/untreated) Rate of Test Compound (mg/g of seed) | | | | |
|---|---|---|---|---|---|
| | 0.10 | 0.25 | 0.50 | 1.00 | 2.00 |
| A | 1.14 | 1.14 | 1.27 | 1.39 | 1.64 |
| B | 1.00 | 1.14 | 1.27 | 1.27 | 1.39 |
| C | 1.14 | 1.14 | 1.39 | 1.52 | 1.64 |

TABLE XXIV-continued

| Test Compound | RATIO (treated/untreated) Rate of Test Compound (mg/g of seed) | | | | |
|---|---|---|---|---|---|
| | 0.10 | 0.25 | 0.50 | 1.00 | 2.00 |
| D | 1.00 | 1.14 | 1.14 | 1.00 | 1.00 |
| E | 1.13 | 1.50 | 1.50 | 1.50 | 1.63 |
| F | 1.25 | 1.13 | 1.13 | 1.25 | 1.13 |
| G | 1.00 | 1.00 | 1.00 | 1.27 | 1.00 |
| H | 1.13 | 1.00 | 1.00 | 1.00 | 1.13 |
| I | 1.00 | 1.00 | 1.27 | 1.27 | 1.27 |
| J | 1.00 | 1.14 | 1.27 | 1.39 | 1.39 |
| K | 1.00 | 1.14 | 1.14 | 1.39 | 1.52 |
| L | 1.27 | 1.27 | 1.50 | 1.50 | 1.77 |
| M | 1.27 | 1.52 | 1.64 | 1.77 | 2.02 |
| N | 1.20 | 1.60 | 1.80 | 1.80 | 1.60 |
| O | 1.14 | 1.29 | 1.29 | 1.43 | 1.43 |
| P | 1.00 | 1.00 | 1.00 | 1.17 | 1.17 |
| Q | 1.33 | 1.33 | 1.17 | 1.17 | 1.00 |
| R | 1.00 | 1.00 | 1.33 | 1.17 | 1.17 |
| S | 1.25 | 1.13 | 1.25 | 1.25 | 1.00 |
| T | 1.00 | 1.33 | 1.33 | 1.83 | 1.50 |
| U | 1.17 | 2.00 | 2.00 | 2.33 | 2.50 |
| V | 1.25 | 1.50 | 1.25 | 1.00 | 1.13 |
| W | 1.00 | 1.50 | 1.63 | 1.50 | 1.25 |
| X | 1.33 | 1.67 | 2.00 | 2.00 | 2.33 |
| Y | — | — | 1.20 | 1.20 | 1.40 |
| Z | 0.86 | 1.00 | 1.43 | 1.43 | 1.43 |
| AA | — | — | 0.80 | 1.20 | 1.40 |
| BB | — | — | 1.20 | 1.20 | 1.00 |

— = no evaluation

EXAMPLE 25

Preparation of 5-[(2-Chloro-α,α,α-trifluoro -p-tolyl)oxy]salicylic acid

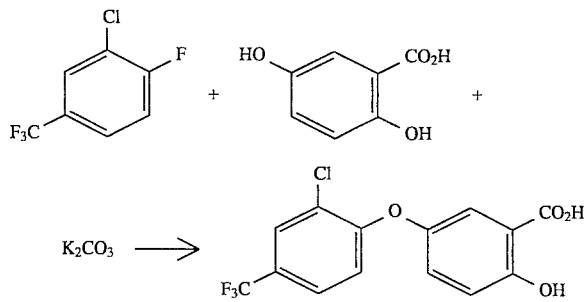

A mixture of 3-chloro-4-fluoro-α,α,α-trifluorotoluene (103 g, 0.52 mol), 2,5-dihydroxybenzoic acid (80 g, 0.52 mol) and potassium carbonate (180 g, 1.3 mol) in dimethyl sulfoxide is heated to and held at 130° C. for about 30 hours, cooled to room temperature and poured into ice-water. The aqueous mixture is acidified to pH 2 with concentrated hydrochloric acid and decanted to obtain an oil. The oil is dissolved in methylene chloride, washed with water and concentrated in vacuo to form a brown oil which is crystallized from ether to give the title product as a tan solid (158 g, 91.3%, mp 135° C.).

Using esentially the same procedure, the following compounds are obtained:

| X | $X_1$ | $X_2$ | $X_3$ | Y | R | mp °C. |
|---|---|---|---|---|---|---|
| Cl | H | $CF_3$ | H | N | OH | 193–195 |
| Cl | H | $CF_3$ | H | CH | $CH_3$ | 82–83 |
| $NO_2$ | H | $CF_3$ | H | CH | OH | 208–210 |
| Cl | H | $CF_3$ | H | CF | OH | 186–187 |
| H | $CF_3$ | H | Cl | CCl | OH | 158–161 |
| Cl | H | $CF_3$ | H | CF | $CH_3$ | 84.5–85 |

EXAMPLE 26

Preparation of Methyl 5-[(2-chloro-α,α,α-trifluoro-p-tolyl)oxy]salicylate

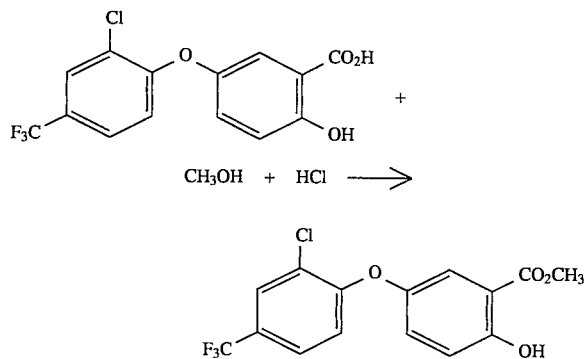

A chilled solution of 5-[(2-chloro-α,α,α-trifluoro-p-tolyl)oxy]salicylic acid (148 g, 0.45 mol) in methanol is saturated with hydrogen chloride gas, warmed to and held at room temperature overnight and poured onto ice. The aqueous mixture is adjusted to about pH 7.5 with concentrated ammonium hydroxide solution and extracted with methylene chloride. The combined organic extracts are washed with saturated sodium bicarbonate solution, dried over anhydrous sodium sulfate, treated with 10 g of silica gel, filtered and concentrated in vacuo to obtain a dark gum. The gum is dissolved in a methanol-water solution, treated with charcoal, filtered and crystallized to give the title product as an offwhite solid (102.3 g 66.2% mp 62°–64° C.).

Using essentially the same procedure, but substituting the appropriately substituted salicylic acid for 5-[(2-chloro-α, α,α-trifluoro-p-tolyl)oxy]salicylic acid, the following compounds are obtained:

| X | $X_1$ | $X_2$ | $X_3$ | Y | mp °C. |
|---|---|---|---|---|---|
| $NO_2$ | H | $CF_3$ | H | CH | 85–86 |
| Cl | H | $CF_3$ | H | CF | 48–50 |
| H | $CF_3$ | H | Cl | CCl | 70–72 |
| Cl | H | $CF_3$ | H | N | |

EXAMPLE 27

Preparation of α-Carboxy-5-[(2-chloro-α,α, α-trifluoro-p-tolyl)oxy]-o-anisic acid, dimethyl ester

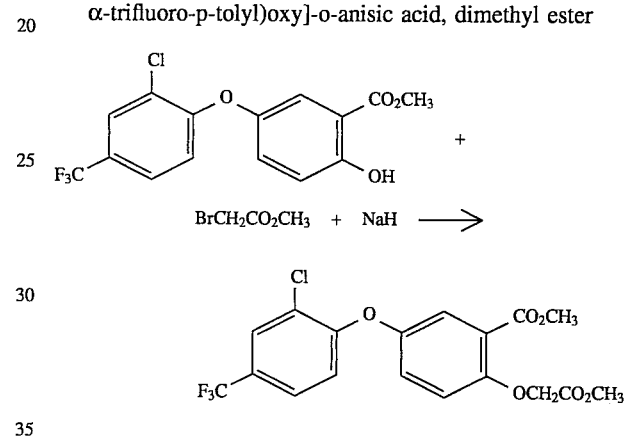

Sodium hydride (60% in oil, 9.44 g, 0.24 mol) is added portionwise over 30 minutes to a solution of methyl 5-[(2-chloro-α,α,α-trifluoro-p-tolyl) oxy]salicylate (74.5 g, 0.22 mol) in N,N-dimethylformamide while maintaining the reaction mixture temperature between 0° and 15° C. After stirring at 0° C. for 1 hour, the reaction mixture is treated dropwise with methyl bromoacetate (38.09 g, 0.25 mol), warmed to and stirred at room temperature for 3 hours, poured into water and extracted with ethyl acetate. The combined organic extracts are washed sequentially with water and brine, dried over anhydrous magnesium sulfate and concentrated in vacuo to obtain an oil. Flash chromatography of the oil using silica gel and 50% to 0% petroleum ether in methylene chloride solutions yields a pale orange oil which is crystallized from petroleum ether to give the title product as a white solid (76.1 g, 84.5%, mp 55°–56° C.).

Using essentially the same procedure, the following compounds are obtained:

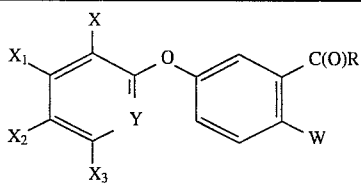

| X | X₁ | X₂ | X₃ | Y | R | W | mp °C. |
|---|----|----|----|---|---|---|--------|
| Cl | H | CF₃ | H | CF | OCH₃ | OCH₂CO₂CH₃ | 103–104 |
| Cl | H | CF₃ | H | CH | OCH₃ | OCH₂CO₂C(CH₃)₃ | 84–85 |
| NO₂ | H | CF₃ | H | CH | CH₃ | OCH₂CO₂CH₃ | 93–94 |
| Cl | H | CF₃ | H | CH | OCH₃ | OCH(CH₃)CO₂CH₃ | 74–77 |
| H | CF₃ | H | Cl | CCl | OCH₃ | OCH₂CO₂CH₃ | 83 |
| Cl | H | CF₃ | H | CH | OCH₃ | O(CH₂)₃CO₂CH₃ | oil |
| Cl | H | CF₃ | H | CH | OCH₃ | OCHCO₂C₂H₅<br>\|<br>CH₂CH₂CH₃ | oil |
| Cl | H | CF₃ | H | CH | OCH₃ | OCH₂C(O)CH₃ | 95–96 |
| Cl | H | CF₃ | H | CH | OCH₃ | O(CH₂)₄CO₂CH₃ | oil |
| Cl | H | CF₃ | H | N | OCH₃ | OCH₂CO₂CH₃ | 68–70 |
| Cl | H | CF₃ | H | CF | CH₃ | OCH₂CO₂CH₃ | 58.5–59.5 |
| Cl | H | CF₃ | H | CH | CH₃ | OCH₂CO₂CH₃ | 100–101 |
| Cl | H | CF₃ | H | CH | OCH₃ | OCHCO₂C₂H₅<br>\|<br>(CH₂)₂—C₆H₅ | oil |
| Cl | H | CF₃ | H | CH | OCH₃ | OCHCO₂C₂H₅<br>\|<br>(CH₂)₄CH₃ | oil |
| Cl | H | CF₃ | H | CH | OCH₃ | OCHCO₂CH₃<br>\|<br>C₆H₅ | oil |
| Cl | H | CF₃ | H | CH | OCH₃ | OCHCO₂CH₃<br>\|<br>C₂H₅ | oil |
| Cl | H | CF₃ | H | CH | OCH₃ | OCHCO₂C₂H₅<br>\|<br>C₂H₅ | oil |
| Cl | H | CF₃ | H | CH | OCH₃ | OCHCO₂C₂H₅<br>\|<br>(CH₂)₁₁CH₃ | oil |
| Cl | H | CF₃ | H | CH | OCH₃ | OCHCO₂C₂H₅<br>\|<br>CH(CH₃)₂ | oil |
| Cl | H | CF₃ | H | CH | OCH₃ | —O—(lactone ring) | oil |

EXAMPLE 28

Preparation of 2-(Carboxymethoxy)-5-[(2-chloro-α,α,α-trifluoro-p-tolyl)oxy]benzoic acid

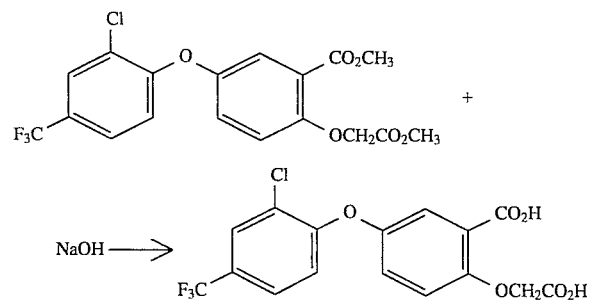

A mixture of α-carboxy-5-[(2-chloro-α,α,α-trifluoro-p-tolyl)oxy]-o-anisic acid, dimethyl ester (5.0 g, 11.9 mmol) and 2N sodium hydroxide solution (20 mL, 40 mmol) in a 1:1 tetrahydrofuran/methanol solution is heated to and held at 50° C. for 2.5 hours, concentrated in vacuo to remove excess tetrahydrofuran, diluted with water and washed with ether. The washed aqueous solution is acidified with concentrated hydrochloric acid and filtered to obtain a solid. A solution of the solid in methylene chloride is dried over anhydrous sodium sulfate and filtered. Hexanes are added to the filtrate until the cloud point is reached. After crystallization occurs, the mixture is filtered to obtain the title product as a white solid (3.26 g, 70%, mp 172°–174° C.).

Using essentially the same procedure, the following compounds are obtained:

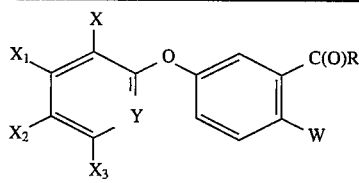

| X | $X_1$ | $X_2$ | $X_3$ | Y | R | W | mp °C. |
|---|---|---|---|---|---|---|---|
| Cl | H | $CF_3$ | H | CF | OH | $OCH_2CO_2H$ | 170–172 |
| H | $CF_3$ | H | Cl | CCl | OH | $OCH_2CO_2H$ | 167–168 |
| Cl | H | $CF_3$ | H | CF | $CH_3$ | $OCH_2CO_2H$ | 136–137 |
| Cl | H | $CF_3$ | H | CH | OH | $O(CH_2)_2CO_2H$ | 210–212 |
| Cl | H | $CF_3$ | H | CH | OH | $OCH(CH_3)CO_2H$ | 141–142 |
| H | H | $CF_3$ | H | CF | OH | $OCH_2CO_2H$ | 139–141 |
| H | H | $CF_3$ | H | CH | OH | $OCH_2CO_2H$ | 141–142 |
| Cl | H | $CF_3$ | H | N | OH | $OCH_2CO_2H$ | 134–136 |
| Cl | H | $CF_3$ | H | CH | $CH_3$ | $OCH_2CO_2H$ | 103 |
| Cl | H | $CF_3$ | H | CH | OH | $OCHCO_2H$<br>\|<br>$CH_2CH_2CH_3$ | 159–160 |
| Cl | H | $CF_3$ | H | CH | OH | $O(CH_2)_4CO_2H$ | 123–124 |
| Cl | H | $CF_3$ | H | CH | OH | $OCHCO_2CH_3$<br>\|<br>$C_2H_5$ | 68–70 |
| Cl | H | $CF_3$ | H | CH | OH | $OCHCO_2H$<br>\|<br>$CH(CH_3)_2$ | 130–131 |
| Cl | H | $CF_3$ | H | CH | OH | $OCHCO_2H$<br>\|<br>$C_2H_5$ | 140–141 |
| Cl | H | $CF_3$ | H | CH | OH | $O(CH_2)_3CO_2H$ | 153–155 |
| Cl | H | $CF_3$ | H | CH | OH | $OCHCO_2H$<br>\|<br>$(CH_2)_2-C_6H_5$ | 117–120 |
| Cl | H | $CF_3$ | H | CH | OH | $OCHCO_2H$<br>\|<br>$(CH_2)_4CH_3$ | 140–141 |
| Cl | H | $CF_3$ | H | CH | OH | $OCHCO_2H$<br>\|<br>$C_6H_5$ | 157–158 |
| Cl | H | $CF_3$ | H | CH | OH | $OCHCO_2H$<br>\|<br>$(CH_2)_{11}CH_3$ | 118–120 |
| Cl | H | $CF_3$ | H | CH | OH | $OCHCO_2H$<br>\|<br>$CH(CH_3)_2$ | 130–131 |
| Cl | H | $CF_3$ | H | CH | OH | lactone ring | 111–113.5 |

EXAMPLE 29

Preparation of 2-(Carboxymethoxy)-5-[(2-chloro-α,α,α-trifluoro-p-tolyl)oxy]benzoic acid, diammonium salt

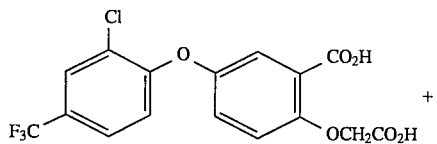

+

$NH_4OH \longrightarrow$ -continued

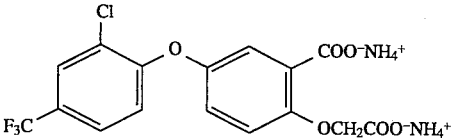

A mixture of 2-(carboxymethoxy)-5-[(2-chloro -α,α,α-trifluoro-p-tolyl)oxy]benzoic acid (2.0 g, 5.12 mmol) and concentrated ammonium hydroxide solution (0.5 mL, 7.25 mmol) in water is stirred until homogeneous and concentrated in vacuo to obtain a residue. A solution of the residue in methanol is brought to the cloud point with ether. The solution is cooled in an ice bath and the solid is collected by filtration to give the title product as a white solid (1.5 g, 72%, mp 226–227).

Using essentially the same procedure, but substituting the appropriately substituted amine or sodium hydroxide for ammonium hydroxide, the following compounds are obtained:

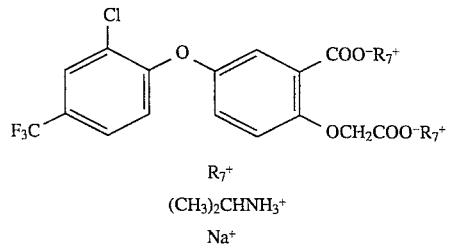

$R_7^+$
$(CH_3)_2CHNH_3^+$
$Na^+$

EXAMPLE 30

Preparation of 2-[(Chloroformyl)methoxy]-5-[(2-chloro-α,α,α-trifluoro-p-tolyl)oxy]benzoyl chloride

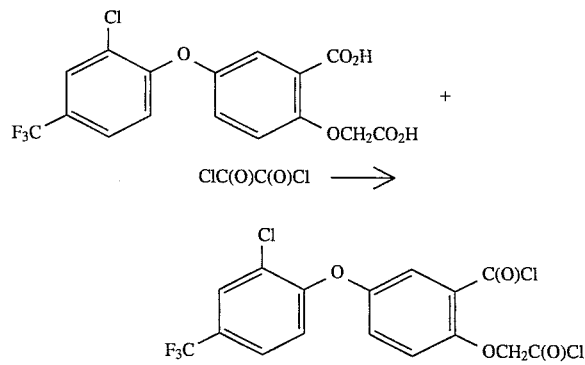

A mixture of 2-(carboxymethoxy)-5-[(2-chloro -α,α,α-trifluoro-p-tolyl)oxy]benzoic acid (16.0 g, 40.95 mmol) in methylene chloride is cooled to −8° C., treated with oxalyl chloride (20.8 g, 163.8 mmol) and four drops of N,N-dimethylformamide, stirred for several minutes and concentrated in vacuo to obtain a solid. The solid is dissolved in toluene and the resultant organic solution is concentrated in vacuo to give the title product as an off-white solid (16.7 g, 95.4%).

Using essentially the same procedure, but substituting 2-(1-carboxybutoxy)-5-[(2-chloro-α,α,α-trifluoro-p-tolyl)oxy]benzoic acid for 2-(carboxymethoxy)-5-[(2-chloro-α, α,α-trifluoro-p-tolyl)oxy]benzoic acid, 2-[1-(chloroformyl-)butoxy]-5-[(2-chloro-α,α,α-trifluoro-p-tolyl)oxy]benzoyl chloride is obtained.

EXAMPLE 31

Preparation of 2-(Carboxyethoxy)-5-[(2-chloro -α,α,α-trifluoro-p-tolyl)oxy]benzoic acid, diallyl ester

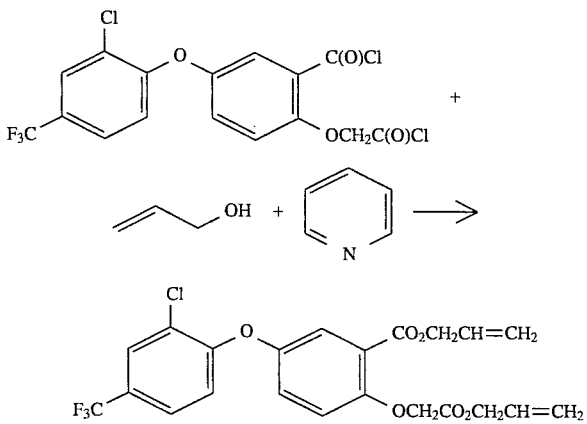

Pyridine (1.7 mL) is added to a mixture of 2-[(chloroformyl)methoxy]-5-[(2-chloro-α,α,α-trifluoro-p-tolyl)oxy] benzoyl chloride (4.16 g, 9.71 mmol) and allyl alcohol (21.36 g, 367 mmol, 25 mL) in tetrahydrofuran. The reaction mixture is stirred at room temperature for one hour and concentrated in vacuo to obtain an oil which is dissolved in ether. The organic solution is washed sequentially with water, 2N hydrochloric acid and brine, dried over anhydrous sodium sulfate and concentrated in vacuo to obtain a solid. Flash column chromatography of the solid using silica gel and a 50% ethyl acetate in hexanes solution affords a gold solid which is recrystallized from an ether/hexanes solution to give the title product as a white solid (1.8 g, mp 36° C.).

Using essentially the same procedure, the following compounds are obtained:

| $R_1$ | $R_7$ |
|---|---|
| H | $C_2H_5$ |
| H | $CH(CH_3)_2$ |
| $CH_2CH_2CH_3$ | $CH_2CH=CH_2$ |
| $CH_2CH_2CH_3$ | $CH_2-C_6H_5$ |

EXAMPLE 32

Preparation of 2-(Carboxymethoxy)-5-[(α,α,α-trifluoro-p-tolyl)oxy]benzoic acid, dimethyl ester

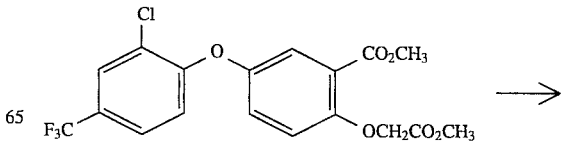

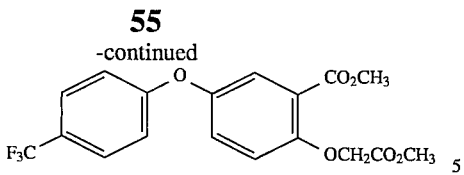

10% Palladium on carbon (1.65 g) is added to a chilled mixture of α-carboxy-5-[(2-chloro-α,α, α-trifluoro-p-tolyl)oxy]-o-anisic acid, dimethyl ester (6.28 g, 15.0 mmol) and ammonium formate (4.73 g, 75.0 mmol) in methanol. The reaction mixture is stirred at room temperature for 4 hours and filtered through diatomaceous earth. The filtrate is concentrated in vacuo to obtain a solid which is diluted with water and extracted with ethyl acetate. The combined organic extracts are dried over anhydrous sodium sulfate and concentrated in vacuo to obtain a white solid. A solution of the solid in methylene chloride and hexanes is treated with silica gel and filtered. The filtrate crystallizes to give the title product as a white solid (3.16 g, 54.9%, mp 84°–85° C.).

EXAMPLE 33

Preparation of 2-(Carboxymethoxy)-5-[(2-chloro-α,α,α-trifluoro-p-tolyl)oxy]benzoic acid, 1-methyl ester

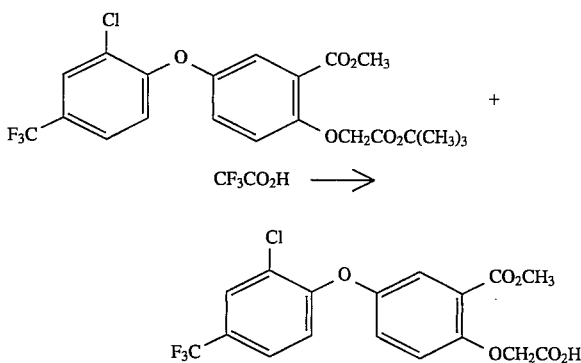

A solution of 2-(carboxymethoxy)-5-[(2-chloro -α,α,α-trifluoro-p-tolyl)oxy]benzoic acid, 2-tert -butyl methyl ester (2.3 g, 4.99 mmol) in methylene chloride is added dropwise to trifluoroacetic acid. The reaction mixture is stirred at room temperature for 2 hours, concentrated in vacuo, diluted with an ether/ice mixture and extracted with saturated sodium bicarbonate solution. The combined aqueous extracts are acidified with concentrated hydrochloric acid and filtered to obtain a white solid. The solid is recrystallized from an ether/hexanes solution to give the title product as a white solid (1.12 g, 55.4%, mp 126°–128° C.).

EXAMPLE 34

Preparation of Methyl 2-amino-5-[(2-chloro -α,α,α-trifluoro-p-tolyl)oxy]benzoate, hydrochloride

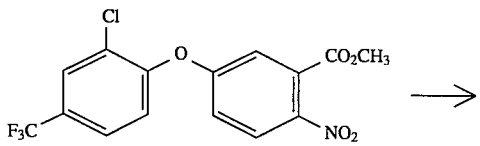

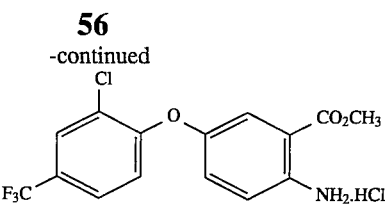

A mixture of 5-[(2-chloro-α,α,α-trifluoro-p -tolyl)oxy]-2-nitrobenzoic acid, methyl ester (15.0 g, 40.0 mmol), 5% palladium on carbon (1.5 g) and concentrated hydrochloric acid (5 mL) in methanol is shaken in a Parr Hydrogenator until 117 psi of hydrogen is taken up. The reaction mixture is then diluted with an acetone/water solution and filtered through diatomaceous earth. The filtrate is concentrated in vacuo to obtain a yellow solid (17.5 g). A sample of the solid (5 g) is dissolved in methanol and crystallized to give the title product as an off-white solid (0.86 g, mp 166°–168° C.).

EXAMPLE 35

Preparation of Methyl 5-[(2-chloro-α,α,α-trifluoro-p-tolyl)oxy]-2-iodobenzoate

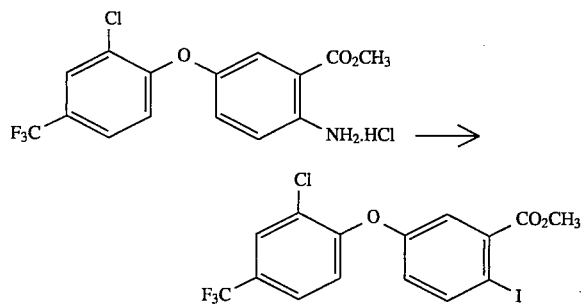

Sodium nitrate (6.32 g, 91.6 mmol) is added portionwise over 25 minutes to a solution of methyl 2-amino-5-[(2-chloro-α,α,α-trifluoro-p-tolyl) oxy]benzoate, hydrochloride (35.0 g, 91.6 mmol) in 1N hydrochloric acid (125 mL) and glacial acetic acid (75 mL) at 0° C. Copper (I) iodide (34.89 g, 183.2 mmol) is then added to the reaction mixture followed by the dropwise addition of 5.5N hydriodic acid (19.95 mL, 109.9 mmol). The resultant brown reaction mixture is heated to and held at 40° C. for 5 minutes, diluted with methylene chloride and filtered. The filtrate is extracted with methylene chloride. The combined organic extracts are washed sequentially with water and saturated sodium bicarbonate solution, dried over anhydrous sodium sulfate and concentrated in vacuo to obtain a dark brown oil. Flash column chromatography of the oil using silica gel and a 5% ether in hexanes solution gives the title product as a gold oil.

EXAMPLE 36

Preparation of 2-Carboxy-4-[(2-chloro-α, α,α-trifluoro-p-tolyl)oxy]cinnamic acid, dimethyl ester

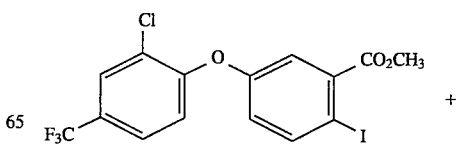

-continued $H_2C=CHCO_2CH_3$ + $Pd(OCCH_3)$ + 
$(C_6H_5)_3P$ + $(C_2H_5)_3N$ ⟶

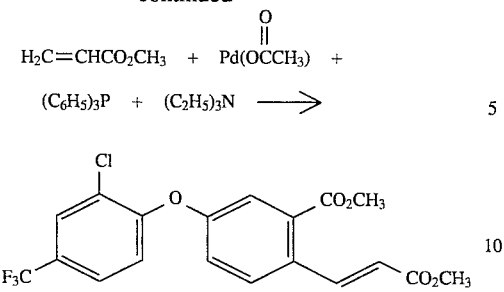

Methyl acrylate (12.8 g, 148.7 mmol) is added to a mixture of methyl 5-[(2-chloro-α,α,α-trifluoro-p-tolyl)oxy] -2-iodobenzoate (13.58 g, 29.74 mmol), palladium (II) acetate (0.08 g, 0.36 mmol), triphenyl phosphine (0.31 g, 1.2 mmol) and triethylamine (7.52 g, 74.32 mmol). The reaction mixture is heated for several hours at 115° C. in a Parr Bomb and filtered to remove solids. The filtrate is concentrated in vacuo to obtain a gold solid which is recrystallized from an ether/hexanes solution to give the title product as a yellow solid (7.79 g, mp 95°–97° C.).

What is claimed is:

1. A method for protecting cereal crops from injury caused by a herbicidally effective amount of a herbicide which comprises applying to the cereal crop plant, the seed of the cereal crop, or the soil or water surrounding the cereal crop or cereal crop seed an effective antidotal amount of a safener compound having the structural formula

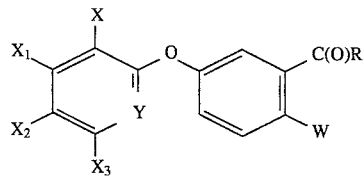

wherein

Y is N or $CX_4$;

X, $X_1$, $X_2$, $X_3$ and $X_4$ are each independently hydrogen, halogen, $C_1$–$C_4$alkyl, $C_1$–$C_4$haloalkyl, $C_1$–$C_4$alkoxy or $C_1$–$C_4$haloalkoxy;

W is $O(CR_1R_2)_nC(O)R_3$, $CR_4$=$CR_5C(O)R_6$ or

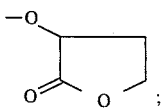

R, $R_3$ and $R_6$ are each independently $OR_7$ or $R_8$;

$R_7$ is hydrogen, $C_1$–$C_4$alkyl, $C_2$–$C_6$alkenyl, $C_2$–$C_6$alkynyl, furfuryl,
 benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or
 an alkali metal, alkaline earth metal, manganese, copper, zinc, cobalt, silver, nickel, ammonium or organic ammonium cation;

$R_8$ is hydrogen, $C_1$–$C_4$alkyl, $C_2$–$C_6$alkenyl, $C_2$–$C_6$alkynyl,
 phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or
 benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_1$ is hydrogen, halogen,
 phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or
 $C_1$–$C_{12}$alkyl optionally substituted with phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_2$, $R_4$ and $R_5$ are each independently hydrogen, halogen or $C_1$–$C_4$alkyl;

n is an integer of 1, 2, 3 or 4; or when $R_1$ and $R_2$ are not the same, the optical isomers thereof.

2. The method according to claim 1 wherein

Y is $CX_4$;

X, $X_1$, $X_2$, $X_3$ and $X_4$ are each independently hydrogen, halogen or $C_1$–$C_4$haloalkyl;

W is $O(CR_1R_2)C(O)R_3$;

R is $OR_7$;

$R_8$ is $C_1$–$C_4$alkyl;

$R_1$ is hydrogen, halogen, phenyl or
 $C_1$–$C_{12}$alkyl optionally substituted with phenyl; and $R_2$ is hydrogen or $C_1$–$C_4$alkyl.

3. The method according to claim 2 wherein

X, $X_3$ and $X_4$ are each independently hydrogen or halogen;

$X_1$ and $X_2$ are each independently hydrogen, halogen or $CF_3$;

W is $O(CHR_1)C(O)R_3$;

$R_7$ is hydrogen, $C_1$–$C_4$alkyl, $C_2$–$C_6$alkenyl or
 an alkali metal, alkaline earth metal, manganese, copper, zinc, cobalt, silver, nickel, ammonium or organic ammonium cation; and $R_1$ is hydrogen or C1-C6alkyl optionally substituted with phenyl.

4. The method according to claim 3 wherein the safener compound is

α-carboxy-5-[(2-chloro-α,α,α-trifluoro -p-tolyl)oxy]-o-anisic acid, dimethyl ester;

2-(1-carboxybutoxy)-5-[(2-chloro-α, α,α-trifluoro-p-tolyl)oxy]benzoic acid;

2-(1-carboxyethoxy)-5-[(2-chloro-α, α,α-trifluoro-p-tolyl)oxy]benzoic acid; or 2-(carboxymethoxy)-5-[(5,6-dichloro-α,α, α-trifluoro-m-tolyl)oxy]benzoic acid, dimethyl ester.

5. The method according to claim 1 wherein the cereal crop is corn, the herbicide is selected from the group consisting of an imidazolinone compound, a dinitroaniline compound, a sulfonylurea compound, a sulfamoylurea compound, an oxime compound, a 2-(4-aryloxyphenoxy)propionic acid compound, a thiocarbamate compound, a 2-chloroacetanilide compound and an isoxazolyl-2-imidazolidinone compound, and the safener compound is applied to the corn plant or seed of the corn.

6. The method according to claim 5 wherein the herbicide is an imidazolinone compound selected from the group consisting of 5-ethyl-2-(4-isopropyl-4-methyl-5-oxo-2-imidazolin-2-yl)nicotinic acid;

2-(4-isopropyl-4-methyl-5-oxo-2-imidazolin-2-yl)-3-quinolinecarboxylic acid;

methyl 2-(4-isopropyl-4-methyl-5-oxo-2-imidazolin-2-yl)nicotinate;

2-(4-isopropyl-4-methyl-5-oxo-2-imidazolin-2-yl)-5-(methoxymethyl)nicotinic acid;

mixture of methyl 2-(4-isopropyl-4-methyl-5-oxo-2-imidazolin-2-yl)-p-toluate and methyl 6-(4-isopropyl-4-methyl-5-oxo-2-imidazolin-2-yl)-m-toluate; and 2-(4-isopropyl-4-methyl-5-oxo-2-imidazolin-2-yl)-5-methylnicotinic acid.

7. The method according to claim 6 wherein the imidazolinone compound is 5-ethyl-2-(4-isopropyl-4-methyl-5-oxo-2-imidazolin-2-yl)nicotinic acid or 2-(4-isopropyl-4-methyl-5-oxo-2-imidazolin-2-yl)-5-methylnicotinic acid.

8. The method according to claim 1 wherein the cereal crop is wheat, barley or sorghum, the herbicide is selected from the group consisting of an imidazolinone compound, a dinitroaniline compound, a sulfonylurea compound, a sulfamoylurea compound, an oxime compound, a 2-(4-aryloxyphenoxy)propionic acid compound, a 2-chloroacetanilide compound and an isoxazolyl-2-imidazolidinone compound, and the safener compound is applied to the seed of the wheat, barley or sorghum.

9. The method according to claim 8 wherein the cereal crop is wheat and the herbicide is a dinitroaniline.

10. The method according to claim 9 wherein the dinitroaniline is N-(1-ethylpropyl)-2,6-dinitro-3,4-xylidine.

11. The method according to claim 1 wherein the cereal crop is wheat, barley or sorghum, the herbicide is selected from the group consisting of an imidazolinone compound, a sulfonylurea compound, a sulfamoylurea compound, an oxime compound, a 2-(4-aryloxyphenoxy) propionic acid compound and an isoxazolyl-2-imidazolidinone compound, and the safener compound is applied to the crop plant.

12. The method according to claim 11 wherein the cereal crop is wheat and the herbicide is selected from the group consisting of an imidazolinone compound, a sulfamoylurea compound, a 2-(4-aryloxyphenoxy)propionic acid compound and an isoxazolyl-2-imidazolidinone compound.

13. The method according to claim 1 wherein the cereal crop is rice or oats, the herbicide is selected from the group consisting of an imidazolinone compound, a sulfonylurea compound, a sulfamoylurea compound, an oxime compound, a 2-(4-aryloxyphenoxy) propionic acid compound and an isoxazolyl-2-imidazolidinone compound, and the safener compound is applied to the cereal crop plant or seed of the cereal crop plant.

14. The method according to claim 13 wherein the cereal crop is rice and the herbicide is selected from the group consisting of an imidazolinone compound, a sulfonylurea compound, a sulfamoylurea compound, an oxime compound and a 2-(4-aryloxyphenoxy)propionic acid compound.

15. A compound having the structural formula

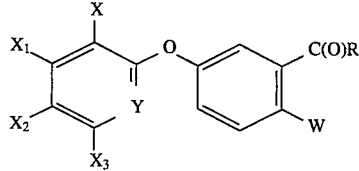

wherein

Y is N or $CX_4$;

X, $X_1$, $X_2$, $X_3$ and $X_4$ are each independently hydrogen, halogen, $C_1$–$C_4$alkyl, $C_1$–$C_4$haloalkyl, $C_1$–$C_4$alkoxy or $C_1$–$C_4$haloalkoxy;

W is $O(CR_1R_2)_nC(O)R_3$, $CR_4$=$CR_5C(O)R_6$ or

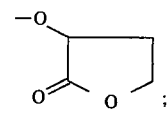

R, $R_3$ and $R_6$ are each independently $OR_7$ or $R_8$;

$R_7$ is hydrogen, $C_1$–$C_4$alkyl, $C_2$–$C_6$alkenyl, $C_2$–$C_6$alkynyl, furfuryl, benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or an alkali metal, alkaline earth metal, manganese, copper, zinc, cobalt, silver, nickel, ammonium or organic ammonium cation;

$R_8$ is hydrogen, $C_1$–$C_4$alkyl, $C_2$–$C_6$alkenyl, $C_2$–$C_6$alkynyl, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or benzyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_1$ is hydrogen, halogen, phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $C_1$–$C_{12}$alkyl optionally substituted with phenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

$R_2$, $R_4$ and $R_5$ are each independently hydrogen, halogen or $C_1$–$C_4$alkyl;

n is an integer of 1, 2, 3 or 4; or when $R_1$ and $R_2$ are not the same, the optical isomers thereof;

provided that when $R_1$ is hydrogen or $C_1$–$C_6$alkyl, $R_2$ is hydrogen or $C_1$–$C_4$alkyl and $R_3$ is $O(C_1$–$C_4$alkyl), R is other than $O(C_1$–$C_4$alkyl).

16. The compound according to claim 17 wherein

Y is $CX_4$;

X, $X_1$, $X_2$, $X_3$ and $X_4$ are each independently hydrogen, halogen or $C_1$–$C_4$haloalkyl;

W is $O(CR_1R_2)C(O)R_3$;

R is $OR_7$;

$R_8$ is $C_1$–$C_4$alkyl;

$R_1$ is hydrogen, halogen, phenyl or $C_1$–$C_{12}$alkyl optionally substituted with phenyl; and $R_2$ is hydrogen or $C_1$–$C_4$alkyl.

17. The compound according to claim 16 wherein

X, $X_3$ and $X_4$ are each independently hydrogen or halogen;

$X_1$ and $X_2$ are each independently hydrogen, halogen or $CF_3$;

W is $O(CHR_1)C(O)R_3$;

$R_7$ is hydrogen, $C_1$–$C_4$alkyl, $C_2$–$C_6$alkenyl or an alkali metal, alkaline earth metal, manganese, copper, zinc, cobalt, silver, nickel, ammonium or organic ammonium cation; and $R_1$ is hydrogen or $C_1$–$C_6$alkyl optionally substituted with phenyl.

18. The compound according to claim 17 wherein the compound is selected from the group consisting of 2-(1-carboxybutoxy)-5-[(2-chloro-α,α,α-trifluoro-p-tolyl)oxy]benzoic acid;

2-(1-carboxyethoxy)-5-[(2-chloro-α,α,α-trifluoro-p-tolyl)oxy]benzoic acid;

5-[(2-chloro-α,α,α-trifluoro-p-tolyl)oxy]-2-(2-oxopropoxy)benzoic acid, methyl ester;

2-(carboxymethoxy)-5-[(5,6-dichloro-α,α,α-trifluoro-m-tolyl)oxy]benzoic acid;

2-(carboxymethoxy)-5-[(α,α,α-trifluoro-p-tolyl)oxy]benzoic acid;

2-(carboxymethoxy)-5-[(2-chloro-α,α,α-trifluoro-p-tolyl)oxy]benzoic acid, diallyl ester;

2-[(1-carboxyhexyl)oxy]-5-[(2-chloro-α,α,α-trifluoro-p-tolyl)oxy]benzoic acid;

2-(1-carboxy-3-phenylpropoxy)-5-[(2-chloro-α,α,α-trifluoro-p-tolyl)oxy]benzoic acid;

2-(1-carboxy-2-methylpropoxy)-5-[(2-chloro-α,α,α-trifluoro-p-tolyl)oxy]benzoic acid; and 2-(1-carboxypropoxy)-5-[(2-chloro-α,α,α-trifluoro-p-tolyl)oxy]benzoic acid.

19. A safener composition comprising an agronomically acceptable inert solid or liquid carrier and 0.5% to 95% by weight of a safener compound as defined in claim 15.

20. A safener composition according to claim 19 wherein the safener compound is selected from the group consisting of 2-(1-carboxybutoxy)-5-[(2-chloro-α,α-trifluoro-p-tolyl)oxy]benzoic acid;

2-(1-carboxyethoxy)-5-[(2-chloro-α,α-trifluoro-p-tolyl)oxy]benzoic acid;

5-[(2-chloro-α,α,α-trifluoro-p-tolyl)oxy]-2-(2-oxopropoxy)benzoic acid, methyl ester;

2-(carboxymethoxy)-5-[(5,6-dichloro-α,α,α-trifluoro-m-tolyl)oxy]benzoic acid;

2-(carboxymethoxy)-5-[(α,α,α-trifluoro-p-tolyl)oxy]benzoic acid;

2-(carboxymethoxy)-5-[(2-chloro-α,α,α-trifluoro-p-tolyl)oxy]benzoic acid, diallyl ester;

2-[(1-carboxyhexyl)oxy]-5-[(2-chloro-α,α,α-trifluoro-p-tolyl)oxy]benzoic acid;

2-(1-carboxy-3-phenylpropoxy)-5-[(2-chloro-α,α,α-trifluoro-p-tolyl)oxy]benzoic acid;

2-(1-carboxy-2-methylpropoxy)-5-[(2-chloro-α,α,α-trifluoro-p-tolyl)oxy]benzoic acid; and 2-(1-carboxypropoxy)-5-[(2-chloro-α,α-trifluoro-p-tolyl)oxy]benzoic acid.

\* \* \* \* \*